(12) United States Patent
Cawthon

(10) Patent No.: US 9,689,028 B2
(45) Date of Patent: Jun. 27, 2017

(54) MONOCHROME MULTIPLEX QUANTITATIVE PCR

(75) Inventor: Richard M. Cawthon, Salt Lake City, UT (US)

(73) Assignee: UNIVERSITY OF UTAH FOUNDATION, Salt Lake City, UT (US)

( * ) Notice: Subject to any disclaimer, the term of this patent is extended or adjusted under 35 U.S.C. 154(b) by 1662 days.

(21) Appl. No.: 13/141,429

(22) PCT Filed: Dec. 22, 2009

(86) PCT No.: PCT/US2009/069243
§ 371 (c)(1),
(2), (4) Date: Aug. 15, 2011

(87) PCT Pub. No.: WO2010/075413
PCT Pub. Date: Jul. 1, 2010

(65) Prior Publication Data
US 2011/0294676 A1    Dec. 1, 2011

Related U.S. Application Data

(60) Provisional application No. 61/139,890, filed on Dec. 22, 2008.

(51) Int. Cl.
C12P 19/34 (2006.01)
C12Q 1/68 (2006.01)

(52) U.S. Cl.
CPC .......... *C12Q 1/6851* (2013.01); *C12Q 1/686* (2013.01)

(58) Field of Classification Search
CPC ............ C12Q 2563/173; C12Q 1/6851; C12Q 1/686; C12Q 2525/155; C12Q 2527/107; C12Q 2537/143; C12Q 2545/101; C12Q 1/6876; C12Q 1/6883; C12Q 1/6886; C12Q 2600/118
See application file for complete search history.

(56) References Cited

U.S. PATENT DOCUMENTS

| | | | |
|---|---|---|---|
| 5,489,508 A | 2/1996 | West et al. | |
| 5,686,245 A | 11/1997 | West | 435/6 |
| 5,741,677 A | 4/1998 | Kozlowski | 435/91.2 |
| 5,741,678 A | 4/1998 | Ronai | 435/912 |
| 5,834,193 A | 11/1998 | Kozlowski et al. | |
| 5,856,096 A | 1/1999 | Windle et al. | |
| 6,020,124 A | 2/2000 | Sorenson | 435/6 |
| 6,436,677 B1 | 8/2002 | Gu | 435/183 |
| 7,695,904 B2 * | 4/2010 | Cawthon | C12Q 1/6853 435/6.13 |
| 8,039,215 B2 * | 10/2011 | Higuchi et al. | 435/6.12 |
| 8,048,631 B2 | 11/2011 | Cawthon | 435/6.12 |
| 2003/0162209 A1 * | 8/2003 | Martin | 435/6 |
| 2003/0162266 A1 | 8/2003 | Cawthon | 435/6 |
| 2004/0175733 A1 * | 9/2004 | Andersen et al. | 435/6 |
| 2006/0141492 A1 * | 6/2006 | Sowers et al. | 435/6 |
| 2006/0210980 A1 | 9/2006 | Cawthon | 435/6 |
| 2011/0020712 A1 | 1/2011 | Angell et al. | 435/6 |
| 2011/0207128 A1 | 8/2011 | Cawthon | 435/6 |
| 2011/0294676 A1 | 12/2011 | Cawthon | |
| 2012/0252014 A1 | 10/2012 | Loeffert et al. | |
| 2013/0011918 A1 | 1/2013 | West et al. | |
| 2014/0248622 A1 | 9/2014 | Wang et al. | |
| 2014/0370505 A1 | 12/2014 | Harley | |

FOREIGN PATENT DOCUMENTS

| | | |
|---|---|---|
| AU | 2003208902 | 1/2003 |
| AU | 2009329987 | 7/2010 |
| CA | 2474468 | 1/2003 |
| CA | 2513747 | 1/2004 |
| CA | 2748265 | 7/2010 |
| CN | 03804867.1 | 1/2003 |
| CN | 2009801572698 | 7/2010 |
| DE | 03707624.7 | 1/2003 |
| EP | 03707624.7 | 1/2003 |
| EP | 04705326.9 | 1/2004 |
| EP | 12152681.8 | 1/2004 |
| EP | 2379747 | 7/2010 |
| ES | 03707624.7 | 1/2003 |
| FR | 03707624.7 | 1/2003 |
| GB | 03707624.7 | 1/2003 |
| HK | 05103554.7 | 1/2003 |
| HK | 1169683 A | 7/2010 |
| IT | 03707624.7 | 1/2003 |
| JP | 09-206081 A | 8/1997 |
| JP | 2003-564211 | 1/2003 |
| JP | 2006-503063 | 1/2004 |
| JP | 2011-543646 | 7/2010 |
| WO | PCT/US1996/010035 | 12/1996 |
| WO | PCT/JP1999/006711 | 6/2001 |
| WO | WO 01/66799 | 9/2001 |
| WO | PCT/US2003/002844 | 1/2003 |
| WO | PCT/US2004/002215 | 1/2004 |
| WO | WO 2006/110735 | 10/2006 |
| WO | WO 2010/075413 | 7/2010 |

OTHER PUBLICATIONS

Bakaysa, S.L. et al. (2007) Telomere length predicts survival independent of genetic influences. Aging Cell. (6): 769-774.

(Continued)

*Primary Examiner* — Cynthia B Wilder

(74) *Attorney, Agent, or Firm* — Ballard Spahr LLP

(57) ABSTRACT

Disclosed herein are methods and compositions for determining the copy number of a first target nucleic acid as compared to the copy number of a second target nucleic acid in a single well with a single detection label. For example, disclosed herein are methods and compositions for determining the copy number of a first target nucleic acid as compared to the copy number of a second target nucleic acid by a monochrome multiplex quantitative PCR (MMQPCR) in a single well with a single detection label.

34 Claims, 7 Drawing Sheets

(56) References Cited

OTHER PUBLICATIONS

D'Aquila, R.T. et al. (1991) Maximizing sensitivity and specificity of PCR by pre-amplification heating. Nucleic Acid Research. 19(13): 3749.
Don, R.H. et al. (1991) 'Touchdown' PCR to circumvent spurious priming during gene amplification. Nucleic Acid Research. 19(14): 4008.
Ehrlenbach, S. et al. (2009) Influences on the reduction of relative telomere length over 10 years in the population-based Bruneck study: introduction of a well-controlled high-throughput assay. Intl. J. Epidemol. (38): 1725-1734.
Fitzpatrick, A.L. (2011) et al., Leukocyte telomere length and mortality in the cardiovascular health study. J. Gerontol. A. Biol. Sci. Med. Sci. 66A(4): 421-429.
Henderson, S. et al. (1996) In situ analysis of changes in telomere size during replicative aging and cell transformation. J. Cell Biol. 134(1): 1-12.
Kimura, M. et al. (2008) Telomere length and mortality: a study of leukocytes in elderly Danish twins. Am. J. Epidemol. 167(7): 799-806.
Kuniaki, A. et al. (2002) Two independent regions of human telomerase reverse transcriptase are important for its oligomerization and telomerase activity. J. Biol. Chem. 277(10): 8538-8544.
Kuramoto, M. et al. (2001) Identification and analyses of the Xenopus TERT gene that encodes the catalytic subunit of telomerase. Gene. 277: 101-110.
Loffert, D. et al. (1997) PCR optimization: primer design. Qiagen News. 5: 3-6.
Masaki, Y. et al. (2002) Telomerase activity detected in eyed embryos of rainbow trout Oncorhynchus mykiss. Fisheries Science. 68: 132-137.
Mather, K.A. et al. (2011) Is telomere length a biomarker of aging? A review. J. Gerontol. A. Biol. Sci. Med. Sci. 66A(2): 202-213.
Nakayama J.I. et al. (2002-03) Stretch PCR Assay. Methods in Molecular Biology. 191: 125-136.
Rufer, N. et al. (1999) Telomere fluorescence measurements in granulocytes and T lymphocyte subsets point to a high turnover of hematopoietic stem cells and memory T cells in early childhood. J. Exp. Med. 190(2): 157-167.
Tatematsu, K. et al. (1996) A novel quantitative 'stretch PCR assay', that detects a dramatic increase in telomerase activity during the progression of myeloid leukemias. Oncogene. 13: 2265-2274.
Office Action issued on Mar. 8, 2011 for Canadian application No. 2513747, which claims priority to PCT/US2004/002215, filed on Jan. 26, 2004. (Applicant—University of Utah; Inventor—Cawthon et al.) (3 pages).
Response to Office Action filed on Sep. 8, 2011 for Canadian application No. 2513747, which claims priority to PCT/US2004/002215, filed on Jan. 26, 2004. (Applicant—University of Utah; Inventor—Cawthon et al.) (23 pages).
Office Action issued on Apr. 16, 2012 for Canadian application No. 2513747, which claims priority to PCT/US2004/002215, filed on Jan. 26, 2004. (Applicant—University of Utah; Inventor—Cawthon et al.) (3 pages).
Office Action issued on Jan. 22, 2010 for European application No. 04705326.9, which claims priority to PCT/US2004/002215, filed on Jan. 26, 2004. (Applicant—University of Utah; Inventor—Cawthon et al.) (6 pages).
Response to Office Action filed on Jun. 21, 2010 for European application No. 04705326.9, which claims priority to PCT/US2004/002215, filed on Jan. 26, 2004. (Applicant—University of Utah; Inventor—Cawthon et al.) (6 pages).
Office Action issued on Dec. 27, 2011 for European application No. 04705326.9, which claims priority to PCT/US2004/002215, filed on Jan. 26, 2004. (Applicant—University of Utah; Inventor—Cawthon et al.) (7 pages).
Office Action issued Feb. 21, 2012 for European application No. 04705326.9, which claims priority to PCT/US2004/002215, filed on Jan. 26, 2004. (Applicant—University of Utah; Inventor—Cawthon et al.) (2 pages).
Response to Office Action filed Apr. 30, 2012 for European application No. 04705326.9, which claims priority to PCT/US2004/002215, filed on Jan. 26, 2004. (Applicant—University of Utah; Inventor—Cawthon et al.) (1 page).
Supplementary Search Report issued on Jun. 19, 2012 for European application No. 04705326.9, which claims priority to PCT/US2004/002215, filed on Jan. 26, 2004. (Applicant—University of Utah; Inventor—Cawthon et al.) (5 pages).
Response to Office Action filed on Jul. 2, 2012 for European application No. 04705326.9, which claims priority to PCT/US2004/002215, filed on Jan. 26, 2004. (Applicant—University of Utah; Inventor—Cawthon et al.) (2 pages).
Intention to Grant issued Sep. 4, 2012 for European application No. 04705326.9, which claims priority to PCT/US2004/002215, filed on Jan. 26, 2004. (44 pages).
Office Action issued Feb. 16, 2012 for European application No. 12152681.8, which claims priority to PCT/US2004/002215, filed on Jan. 26, 2004. (Applicant—University of Utah; Inventor—Cawthon et al.) (1 page).
Response to Office Action filed Apr. 26, 2012 for European application No. 12152681.8, which claims priority to PCT/US2004/002215, filed on Jan. 26, 2004. (Applicant—University of Utah; Inventor—Cawthon et al.) (1 page).
Office Action issued on Apr. 27, 2012 for European application No. 12152681.8, which claims priority to PCT/US2004/002215, filed on Jan. 26, 2004. (Applicant—University of Utah; Inventor—Cawthon et al.) (2 pages).
Response to Office Action filed May 14, 2012 for European application No. 12152681.8, which claims priority to PCT/US2004/002215, filed on Jan. 26, 2004. (Applicant—University of Utah; Inventor—Cawthon et al.) (1 page).
Supplementary Search Report issued on Jun. 8, 2012 for European application No. 12152681.8, which claims priority to PCT/US2004/002215, filed on Jan. 26, 2004. (Applicant—University of Utah; Inventor—Cawthon et al.) (11 pages).
Communication pursuant to Rules 70(2) and 70a(2) EPC and reference to Rule 39(1) EPC issued Jul. 16, 2012 for European application No. 12152681.8, which claims priority to PCT/US2004/002215, filed on Jan. 26, 2004. (Applicant—University of Utah; Inventor—Cawthon et al.) (2 pages).
Office Action issued on Nov. 4, 2009 for Japanese application No. 2006-503063, which claims priority to PCT/US2004/002215, filed on Jan. 26, 2004. (Applicant—University of Utah; Inventor—Cawthon et al.) (2 pages).
Response to Office Action issued on Mar. 25, 2010 for Japanese application No. 2006-503063, which claims priority to PCT/US2004/002215, filed on Jan. 26, 2004. (Applicant—University of Utah; Inventor—Cawthon et al.) (4 pages).
Office Action issued on Nov. 16, 2010 for Japanese application No. 2006-503063, which claims priority to PCT/US2004/002215, filed on Jan. 26, 2004. (Applicant—University of Utah; Inventor—Cawthon et al.) (2 pages).
Notice of appeal filed Mar. 16, 2011 for Japanese application No. 2006-503063, which claims priority to PCT/US2004/002215, filed on Jan. 26, 2004. (Applicant—University of Utah; Inventor—Cawthon et al.) (3 pages).
Formality office action issued Apr. 12, 2011 for Japanese application No. 2006503063, which claims priority to PCT/US2004/002215, filed on Jan. 26, 2004. (2 pages).
Appeal brief filed May 24, 2011 for Japanese application No. 2006-503063, which claims priority to PCT/US2004/002215, filed on Jan. 26, 2004. (Applicant—University of Utah; Inventor—Cawthon et al.) (8 pages).
International search report issued Nov. 18, 2004 for PCT/US2004/002215, filed on Jan. 26, 2004. (Applicant—University of Utah; Inventor—Cawthon et al.) (4 pages).
Written opinion of international search report issued Jul. 24, 2005 for PCT/US2004/002215, filed on Jan. 26, 2004. (Applicant—University of Utah; Inventor—Cawthon et al.) (5 pages).

(56) References Cited

OTHER PUBLICATIONS

International preliminary report on patentability issued on Jul. 29, 2005 for PCT/US2004/002215, filed on Jan. 26, 2004. (Applicant—University of Utah; Inventor—Cawthon et al.) (6 pages).
Preliminary Amendment filed on Mar. 10, 2006 for U.S. Appl. No. 10/543,111, filed Mar. 10, 2006. (Applicant—University of Utah; Inventor—Cawthon et al.) (10 pages).
Office Action issued on Aug. 23, 2007 for U.S. Appl. No. 10/543,111, filed Mar. 10, 2006. (Applicant—University of Utah; Inventor—Cawthon et al.) (13 pages).
Response to Office Action filed on Feb. 25, 2008 for U.S. Appl. No. 10/543,111, filed Mar. 10, 2006. (Applicant—University of Utah; Inventor—Cawthon et al.) (8 pages).
Office Action issued on May 12, 2008 for U.S. Appl. No. 10/543,111, filed Mar. 10, 2006. (Applicant—University of Utah; Inventor—Cawthon et al.) (10 pages).
Response to Office Action filed on Nov. 12, 2008 for U.S. Appl. No. 10/543,111, filed Mar. 10, 2006. (Applicant—University of Utah; Inventor—Cawthon et al.) (6 pages).
Final Office Action issued on Jan. 27, 2009 for U.S. Appl. No. 10/543,111, filed Mar. 10, 2006. (Applicant—University of Utah; Inventor—Cawthon et al.) (10 pages).
Notice of Appeal filed on Jul. 27, 2009 for U.S. Appl. No. 10/543,111, filed Mar. 10, 2006. (Applicant—University of Utah; Inventor—Cawthon et al.) (1 page).
Response to Final Office Action filed on Nov. 25, 2009 for U.S. Appl. No. 10/543,111, filed Mar. 10, 2006. (Applicant—University of Utah; Inventor—Cawthon et al.) (15 pages).
National Phase Entry on Aug. 22, 2011 for Chinese application No. 200980157269.8, which claims priority to PCT/US2009/069243, filed on Dec. 22, 2009. (Applicant—University of Utah; Inventor—Cawthon et al.) (1 page).
Notice of Amendment and Completion of Formalities issued on Sep. 29, 2011 for Chinese application No. 200980157269.8, which claims priority to PCT/US2009/069243, filed on Dec. 22, 2009. (Applicant—University of Utah; Inventor—Cawthon et al.) (3 pages).
Response to Notice of Amendment and Completion of Formalities issued on Jan. 19, 2012 for Chinese application No. 200980157269.8, which claims priority to PCT/US2009/069243, filed on Dec. 22, 2009. (Applicant—University of Utah; Inventor—Cawthon et al.) (2 pages).
Notice of Passing Preliminary Exam issued on Feb. 10, 2012 for Chinese application No. 200980157269.8, which claims priority to PCT/US2009/069243, filed on Dec. 22, 2009. (Applicant—University of Utah; Inventor—Cawthon et al.) (1 page).
Amendment before examination filed on Feb. 13, 2012 for European application No. 09804177.5, which claims priority to PCT/US2009/069243, filed on Dec. 22, 2009. (Applicant—University of Utah; Inventor—Cawthon et al.) (18 pages).
Request for Registration and Grant filed on Oct. 22, 2012 for Hong Kong application No. 12110505.3, which claims priority to PCT/US2009/069243, filed on Dec. 22, 2009. (Applicant—University of Utah; Inventor—Cawthon et al.) (1 page).
International search report issued Mar. 30, 2010 for PCT/US2009/069243, filed on Dec. 22, 2009. (Applicant—University of Utah; Inventor—Cawthon et al.) (5 pages).
Written opinion of international search report issued Jun. 22, 2011 for PCT/US2009/069243, filed on Dec. 22, 2009. (Applicant—University of Utah; Inventor—Cawthon et al.) (5 pages).
International preliminary report on patentability issued on Jun. 22, 2011 for PCT/US2009/069243, filed on Dec. 22, 2009. (Applicant—University of Utah; Inventor—Cawthon et al.) (6 pages).
Request for examination filed on May 3, 2006 for Australian application No. 2003208902, which claims priority to PCT/US2003/002844, filed on Jan. 31, 2003. (Applicant—University of Utah; Inventor—Cawthon et al.)(1 page).
Office Action issued on Mar. 29, 2007 for Australian application No. 2003208902, which claims priority to PCT/US2003/002844, filed on Jan. 31, 2003. (Applicant—University of Utah; Inventor—Cawthon et al.) (2 pages).
Response to Office Action filed on Jul. 23, 2008 for Australian application No. 2003208902, which claims priority to PCT/US2003/002844, filed on Jan. 31, 2003. (Applicant—University of Utah; Inventor—Cawthon et al.) (16 pages).
Notice of Acceptance issued on Jul. 25, 2008 for Australian application No. 2003208902, which claims priority to PCT/US2003/002844, filed on Jan. 31, 2003. (Applicant—University of Utah; Inventor—Cawthon et al.) (7 pages).
Preliminary Amendment filed on Sep. 20, 2004 for Canadian application No. 2474468, which claims priority to PCT/US2003/002844, filed on Jan. 31, 2003. (Applicant—University of Utah; Inventor—Cawthon et al.) (3 pages).
Office Action issued on Jul. 22, 2010 for Canadian application No. 2474468, which claims priority to PCT/US2003/002844, filed on Jan. 31, 2003. (Applicant—University of Utah; Inventor—Cawthon et al.) (4 pages).
Response to Office Action filed on Jan. 20, 2011 for Canadian application No. 2474468, which claims priority to PCT/US2003/002844, filed on Jan. 31, 2003. (Applicant—University of Utah; Inventor—Cawthon et al.) (32 pages).
Office Action issued on Jul. 13, 2011 for Canadian application No. 2474468, which claims priority to PCT/US2003/002844, filed on Jan. 31, 2003. (Applicant—University of Utah; Inventor—Cawthon et al.) (2 pages).
Response to Office Action filed on Jan. 13, 2012 for Canadian application No. 2474468, which claims priority to PCT/US2003/002844, filed on Jan. 31, 2003. (Applicant—University of Utah; Inventor—Cawthon et al.) (15 pages).
Office Action issued on May 29, 2012 for Canadian application No. 2474468, which claims priority to PCT/US2003/002844, filed on Jan. 31, 2003. (Applicant—University of Utah; Inventor—Cawthon et al.) (2 pages).
Office Action issued on Mar. 17, 2006 for Chinese application No. 03804867.1, which claims priority to PCT/US2003/002844, filed on Jan. 31, 2003. (Applicant—University of Utah; Inventor—Cawthon et al.) (4 pages).
Response to Office Action filed on Sep. 19, 2006 for Chinese application No. 03804867.1, which claims priority to PCT/US2003/002844, filed on Jan. 31, 2003. (Applicant—University of Utah; Inventor—Cawthon et al.) (4 pages).
Notice of Acceptance issued on Apr. 1, 2009 for Chinese application No. 03804867.1, which claims priority to PCT/US2003/002844, filed on Jan. 31, 2003. (Applicant—University of Utah; Inventor—Cawthon et al.) (2 pages).
Request for examination filed on Aug. 20, 2004 for European application No. 03707624.7, which claims priority to PCT/US2003/002844, filed on Jan. 31, 2003. (Applicant—University of Utah; Inventor—Cawthon et al.) (7 pages).
Office Action issued on Oct. 26, 2006 for European application No. 03707624.7, which claims priority to PCT/US2003/002844, filed on Jan. 31, 2003. (Applicant—University of Utah; Inventor—Cawthon et al.) (7 pages).
Response to Office Action filed on Aug. 21, 2007 for European application No. 03707624.7, which claims priority to PCT/US2003/002844, filed on Jan. 31, 2003. (Applicant—University of Utah; Inventor—Cawthon et al.) (9 pages).
Office Action issued on Dec. 13, 2007 for European application No. 03707624.7, which claims priority to PCT/US2003/002844, filed on Jan. 31, 2003. (Applicant—University of Utah; Inventor—Cawthon et al.) (6 pages).
Response to Office Action filed on Sep. 17, 2008 for European application No. 03707624.7, which claims priority to PCT/US2003/002844, filed on Jan. 31, 2003. (Applicant—University of Utah; Inventor—Cawthon et al.) (7 pages).
Office Action issued on Oct. 13, 2010 for European application No. 03707624.7, which claims priority to PCT/US2003/002844, filed on Jan. 31, 2003. (Applicant—University of Utah; Inventor—Cawthon et al.) (6 pages).

(56) References Cited

OTHER PUBLICATIONS

Response to Office Action filed on Jan. 18, 2011 for European application No. 03707624.7, which claims priority to PCT/US2003/002844, filed on Jan. 31, 2003. (Applicant—University of Utah; Inventor—Cawthon et al.) (20 pages).
Intention to Grant issued Jun. 6, 2011 for European application No. 03707624.7, which claims priority to PCT/US2003/002844, filed on Jan. 31, 2003. (Applicant—University of Utah; Inventor—Cawthon et al.) (5 pages).
Request for Registration filed on Feb. 11, 2012 for Hong Kong application No. 05103554.7, which claims priority to PCT/US2003/002844, filed on Jan. 31, 2003. (Applicant—University of Utah; Inventor—Cawthon et al.) (1 page).
Certificate of Grant issued Jun. 15, 2012 for Hong Kong application No. 05103554.7, which claims priority to PCT/US2003/002844, filed on Jan. 31, 2003. (Applicant—University of Utah; Inventor—Cawthon et al.) (4 pages).
Request for examination and Preliminary Amendment filed on Jan. 31, 2006 for application No. 2003-564211, which claims priority to PCT/US2003/002844, filed on Jan. 31, 2003. (Applicant—University of Utah; Inventor—Cawthon et al.) (1 page).
Office Action issued on Oct. 7, 2008 for Japanese application No. 2003-564211, which claims priority to PCT/US2003/002844, filed on Jan. 31, 2003. (Applicant—University of Utah; Inventor—Cawthon et al.) (2 pages).
Response to Office Action filed on Apr. 7, 2009 for Japanese application No. 2003564211, which claims priority to PCT/US2003/002844, filed on Jan. 31, 2003. (Applicant—University of Utah; Inventor—Cawthon et al.) (4 pages).
Office Action issued on May 7, 2009 for Japanese application No. 2003-564211, which claims priority to PCT/US2003/002844, filed on Jan. 31, 2003. (Applicant—University of Utah; Inventor—Cawthon et al.) (1 page).
Response to Office Action filed on Sep. 7, 2009 for Japanese application No. 2003564211, which claims priority to PCT/US2003/002844, filed on Jan. 31, 2003. (Applicant—University of Utah; Inventor—Cawthon et al.) (6 pages).
Office Action issued on Nov. 4, 2009 for Japanese application No. 2003-564211, which claims priority to PCT/US2003/002844, filed on Jan. 31, 2003. (Applicant—University of Utah; Inventor—Cawthon et al.) (1 page).
Response to Office Action filed on Apr. 27, 2010 for Japanese application No. 2003564211, which claims priority to PCT/US2003/002844, filed on Jan. 31, 2003. (Applicant—University of Utah; Inventor—Cawthon et al.) (1 page).
Notice of Grant and Translated Claims issued May 21, 2010 for Japanese application No. 2003-564211, which claims priority to PCT/US2003/002844, filed on Jan. 31, 2003. (Applicant—University of Utah; Inventor—Cawthon et al.) (21 pages).
International search report issued Feb. 26, 2004 for PCT/US2003/002844, filed on Jan. 31, 2003. (Applicant—University of Utah; Inventor—Cawthon et al.) (3 pages).
International preliminary report on patentability issued on Jul. 29, 2005 for PCT/US2003/002844, filed on Jan. 31, 2003. (Applicant—University of Utah; Inventor—Cawthon et al.) (3 pages).
Preliminary Amendment filed on Apr. 29, 2003 for U.S. Appl. No. 10/355,626, filed Jan. 31, 2003. (Applicant—University of Utah; Inventor—Cawthon et al.) (9 pages).
Preliminary Amendment filed on Feb. 17, 2005 for U.S. Appl. No. 10/355,626, filed Jan. 31, 2003. (Applicant—University of Utah; Inventor—Cawthon et al.) (9 pages).
Restriction Requirement issued on May 2, 2006 for U.S. Appl. No. 10/355,626, filed Jan. 31, 2003. (Applicant—University of Utah; Inventor—Cawthon et al.) (18 pages).
Response to Restriction Requirement filed on Mar. 2, 2007 for U.S. Appl. No. 10/355,626, filed Jan. 31, 2003. (Applicant—University of Utah; Inventor—Cawthon et al.) (19 pages).
Office Action issued on Aug. 6, 2007 for U.S. Appl. No. 10/355,626, which filed on Jan. 31, 2003. (Applicant—University of Utah; Inventor—Cawthon et al.) (18 pages).
Response to Office Action filed on Jan. 22, 2008 for U.S. Appl. No. 10/355,626, filed Jan. 31, 2003. (Applicant—University of Utah; Inventor—Cawthon et al.) (19 pages).
Office Action issued on Mar. 27, 2008 for U.S. Appl. No. 10/355,626, filed Jan. 31, 2003. (Applicant—University of Utah; Inventor—Cawthon et al.) (18 pages).
Response to Office Action filed on Jun. 27, 2008 for U.S. Appl. No. 10/355,626, filed Jan. 31, 2003. (Applicant—University of Utah; Inventor—Cawthon et al.) (10 pages).
Notice of Appeal filed on Sep. 26, 2008 for U.S. Appl. No. 10/355,626, filed Jan. 31, 2003. (Applicant—University of Utah; Inventor—Cawthon et al.) (1 page).
Advisory Action issued on Oct. 7, 2008 for U.S. Appl. No. 10/355,626, filed Jan. 31, 2003. (Applicant—University of Utah; Inventor—Cawthon et al.) (3 pages).
Office Action issued on Jan. 22, 2009 for U.S. Appl. No. 10/355,626, filed Jan. 31, 2003. (Applicant—University of Utah; Inventor—Cawthon et al.) (8 pages).
Response to Office Action filed on Jul. 22, 2009 for U.S. Appl. No. 10/355,626, filed Jan. 31, 2003. (Applicant—University of Utah; Inventor—Cawthon et al.) (11 pages).
Notice of Allowance issued on Nov. 17, 2009 for U.S. Appl. No. 10/355,626, filed Jan. 31, 2003. (Applicant—University of Utah; Inventor—Cawthon et al.) (6 pages).
Restriction Requirement issued on Jul. 8, 2010 for U.S. Appl. No. 12/700,475, filed Feb. 4, 2010. (Applicant—University of Utah; Inventor—Cawthon et al.) (6 pages).
Response to Restriction Requirement filed on Aug. 9, 2010 for U.S. Appl. No. 12/700,475, filed Feb. 4, 2010. (Applicant—University of Utah; Inventor—Cawthon et al.) (10 pages).
Office Action issued on Oct. 28, 2010 for U.S. Appl. No. 12/700,475, filed Feb. 4, 2010. (Applicant—University of Utah; Inventor—Cawthon et al.) (8 pages).
Response to Office Action filed on Mar. 28, 2011 for U.S. Appl. No. 12/700,475, filed Feb. 4, 2010. (Applicant—University of Utah; Inventor—Cawthon et al.) (14 pages).
Notice of Allowance issued on Jun. 27, 2011 for U.S. Appl. No. 12/700,475, filed Feb. 4, 2010. (Applicant—University of Utah; Inventor—Cawthon et al.)(10 pages).
Almasy L, et al. (1998) Multipoint quantitative-trait linkage analysis in general pedigrees. Am J Hum Genet. 62: 1198-1211.
Beekman M, et al. (2006) Chromosome 4q25, microsomal transfer protein gene, and human longevity: novel data and a meta-analysis of association studies. J Gerontol A Biol Sci Med Sci. 61(4): 355-362.
Blasco MA, et al. (1997) Telomere shortening and tumor formation by mouse cells lacking telomerase RNA. Cell. 91(1): 25-34.
Boulay JL, et al. (1999) Gene dosage by quantitative real-time PCR. Biotechniques. 27(2): 228-230, 232.
Brown MD, et al. (2006) IQGAP1 in cellular signaling: bridging the GAP. Trends Cell Biol. 16(5): 242-249.
Cawthon RM, et al. (2003) Association between telomere length in blood and mortality in people aged 60 years or older. Lancet. 361: 393-395.
Cawthon RM. (2002) Telomere measurement by quantitative PCR. Nucleic Acids Res. 30(10): e47.
Cawthon RM. (2009) Telomere length measurement by a novel monochrome multiplex quantitative PCR method. Nucleic Acids Res. 37(3): e21.
Cheung VG, et al. (2002) The genetics of variation in gene expression. Nat Genet. 32 Suppl: 522-525.
Cheung VG, et al. (2003) Natural variation in human gene expression assessed in lymphoblastoid cells. Nat Genet. 33: 422-425.
Cheung VG, et al. (2005) Mapping determinants of human gene expression by regional and genome-wide association. Nature. 437(7063): 1365-1369.
Dai M, et al. (2005) Evolving gene/transcript definitions significantly alter the interpretation of GeneChip data. Nucleic Acids Res. 33(20): e175.
Dausset J, et al. (1990) Centre d'etude du polymorphisme humain (CEPH): collaborative genetic mapping of the human genome. Genomics. 6(3): 575-577.

(56) References Cited

OTHER PUBLICATIONS

Dixon AL, et al. (2007) A genome-wide association study of global gene expression. Nat Genet. 39(10): 1202-1207.
Dustin ML (2006) Immunology. When F-actin becomes too much of a good thing. Science. 313(5788): 767-768.
Efron B, et al. (2004) Least angle regression. Ann Statist. 32(2): 407-499.
Efron B, et al. (2007) On testing the significance of sets of genes. Ann Appl Stat. 1(1): 107-129.
Foger N, et al. (2006) Requirement for coronin 1 in T lymphocyte trafficking and cellular homeostasis. Science. 313: 839-842.
Frank IE, et al. (1993) A statistical view of some chemometrics regression tools (with discussion). Technometrics. 35: 109-148.
Geesaman BJ, et al. (2003) Haplotype-based identification of a microsomal transfer protein marker associated with the human lifespan. Proc Natl Acad Sci USA. 100(24): 14115-14120.
Goring HH, et al. (2007) Discovery of expression QTLs using large-scale transcriptional profiling in human lymphocytes. Nat Genet. 39(10): 1208-1216.
Hamilton B, et al. (2005) A systematic RNAi screen for longevity genes in C. elegans. Genes Dev. 19(13): 1544-1555.
Haraldsson MK, et al. (2008) The lupus-related Lmb3 locus contains a disease-suppressing Coronin-1A gene mutation. Immunity. 28: 40-51.
Harley CB, et al. (1990) Telomeres shorten during ageing of human fibroblasts. Nature. 345(6274): 458-460.
Herrera E, et al. (1999) Disease states associated with telomerase deficiency appear earlier in mice with short telomeres. EMBO J. 18(11): 2950-2960.
Higuchi R, et al. (1993) Kinetic PCR analysis: real-time monitoring of DNA amplification reactions. Biotechnology (NY). 11(9): 1026-1030.
Hoerl AE, et al. (2000) Ridge regression: Biased estimation for nonorthogonal problems. Technometrics. 41: 80-86.
Hultdin M, et al. (1998) Telomere analysis by fluorescence in situ hybridization and flow cytometry. Nucleic Acids Res. 26(16): 3651-3656.
Johnson MR, et al. (2000) Quantitation of dihydropyrimidine dehydrogenase expression by real-time reverse transcription polymerase chain reaction. Anal Biochem. 278(2): 175-184.
Kainz P. (2000) The PCR plateau phase—towards an understanding of its limitations. Biochim Biophys Acta. 1494: 23-27.
Kerber RA et al. (2001) Familial excess longevity in Utah genealogies. J Gerontol A Biol Sci Med Sci. 56: B130-139.
Kerber RA, et al. (2009) Gene expression profiles associated with aging and mortality in humans. Aging Cell. 8(3): 239-250.
Lawyer FC, et al. (1993) High-level expression, purification, and enzymatic characterization of full-length Thermus aquaticus DNA polymerase and a truncated form deficient in 5' to 3' exonuclease activity. PCR Methods Appl. 2(4): 275-287.
Li B, et al. (2003) Rap1 affects the length and heterogeneity of human telomeres. Mol Biol Cell. 14(12): 5060-5068.
Liu H, et al. (2007) AffyProbeMiner: a web resource for computing or retrieving accurately redefined Affymetrix probe sets. Bioinformatics. 23: 2385-2390.
Liu WM, et al. (2002) Analysis of high density expression microarrays with signed-rank call algorithms. Bioinformatics. 18(12): 1593-1599.
Lunetta KL, et al. (2007) Genetic correlates of longevity and selected age-related phenotypes: a genome-wide association study in the Framingham Study. BMC Med Genet. 8 Suppl 1: S13.
Mathers JC (2006) Nutritional modulation of ageing: genomic and epigenetic approaches. Mech Ageing Dev. 127(6): 584-589.
Mecham BH, et al. (2004) Sequence-matched probes produce increased cross-platform consistency and more reproducible biological results in microarray-based gene expression measurements. Nucleic Acids Res. 32(9): e74.
Merrill RM, et al. (2003) Impact of the LDS church's health doctrine on deaths from diseases and conditions associated with cigarette smoking. Ann Epidemiol. 13(10): 704-711.

Monks SA, et al. (2004) Genetic inheritance of gene expression in human cell lines. Am J Hum Genet. 75(6): 1094-1105.
Morley M, et al. (2004) Genetic analysis of genome-wide variation in human gene expression. Nature. 430(7001): 743-747.
Morrison TB, et al. (1998) Quantification of low-copy transcripts by continuous SYBR Green I monitoring during amplification. Biotechniques. 24(6): 954-958, 960, 962.
Mueller P, et al. (2008) Regulation of T cell survival through coronin-1-mediated generation of inositol-1,4,5-trisphosphate and calcium mobilization after T cell receptor triggering. Nat Immunol. 9(4): 424-431.
Nebel A, et al. (2005) No association between microsomal triglyceride transfer protein (MTP) haplotype and longevity in humans. Proc Natl Acad Sci USA. 102(22): 7906-7909.
O'Callaghan N, et al. (2008) A quantitative real-time PCR method for absolute telomere length. Biotechniques. 44(6): 807-809.
Powers RW, et al. (2006) Extension of chronological life span in yeast by decreased TOR pathway signaling. Genes Dev. 20(2): 174-184.
Puca AA, et al. (2001) A genome-wide scan for linkage to human exceptional longevity identifies a locus on chromosome 4. Proc Natl Acad Sci USA. 98(18): 10505-10508.
Reiner A, et al. (2003) Identifying differentially expressed genes using false discovery rate controlling procedures. Bioinformatics. 19, 368-375.
Ruchaud S, et al. (2007) Chromosomal passengers: conducting cell division. Nat Rev Mol Cell Biol. 8(10): 798-812.
Rudolph KL, et al. (1999) Longevity, stress response, and cancer in aging telomerase-deficient mice. Cell. 96(5): 701-712.
Rufer N, et al. (1998) Telomere length dynamics in human lymphocyte subpopulations measured by flow cytometry. Nat Biotechnol. 16(8): 743-747.
Ryder MI, et al. (2004) Alteration of gene expression profiles of peripheral mononuclear blood cells by tobacco smoke: implications for periodontal diseases. Oral Microbiol Immunol. 19(1): 39-49.
Schadt EE, et al. (2003) Genetics of gene expression surveyed in maize, mouse and man. Nature. 422(6929): 297-302.
Segal MR (2006) Microarray gene expression data with linked survival phenotypes: diffuse large-B-cell lymphoma revisited. Biostatistics. 7, (2): 268-285.
Seong KH, et al. (2001) Application of the gene search system to screen for longevity genes in *Drosophila*. Biogerontology. 2(3): 209-217.
Sheffield VC, et al. (1989) Attachment of a 40-base-pair G + C-rich sequence (GC-clamp) to genomic DNA fragments by the polymerase chain reaction results in improved detection of single-base changes. Proc Natl Acad Sci USA. 86: 232-236.
Shiow LR, et al. (2008) The actin regulator coronin 1A is mutant in a thymic egress-deficient mouse strain and in a patient with severe combined immunodeficiency. Nat Immunol. 9(11): 1307-1315.
Stranger BE, et al. (2005) Genome-Wide Associations of Gene Expression Variation in Humans. PLoS Genet 1(6): e78.
Svenson U, et al. (2008) Breast cancer survival is associated with telomere length in peripheral blood cells. Cancer Res. 68(10): 3618-3623.
Therneau TM. (2007) On mixed-effect Cox models, sparse matrices, and modeling data from large pedigrees. Paper presented on Dec. 31, 2007; available at http://mayoresearch.mayo.edu/mayo/research/biostat/upload/kinship.pdf.
Tibshirani R. (1996) Regression Shrinkage and Selection via the Lasso. Journal of the Royal Statistical Society, Series B. 58(1): 267-288.
van Leeuwen DM, et al. (2005) Differential gene expression in human peripheral blood mononuclear cells induced by cigarette smoke and its constituents. Toxicol Sci. 86(1): 200-210.
Wang L, et al. (2007) Cdc42 GTPase-activating protein deficiency promotes genomic instability and premature aging-like phenotypes. Proc Natl Acad Sci USA. 104(4): 1248-1253.
White R, et al. (1985) Construction of linkage maps with DNA markers for human chromosomes. Nature. 313(5998): 101-105.
Wilson CL, et al. (2004) Amplification protocols introduce systematic but reproducible errors into gene expression studies. Biotechniques. 36(3): 498-506.

(56) References Cited

OTHER PUBLICATIONS

Wittwer CT, et al. (2001) Real-time multiplex PCR assays. Methods. 25(4): 430-442.
Wu Z, et al. (2005) Stochastic models inspired by hybridization theory for short oligonucleotide arrays. J Comput Biol 12(6): 882-893.
Wylie JE, et al. (2003) Biomedical databases: protecting privacy and promoting research. Trends Biotechnol. 21(3): 113-116.
Yang J, et al. (2007) AZD1152, a novel and selective aurora B kinase inhibitor, induces growth arrest, apoptosis, and sensitization for tubulin depolymerizing agent or topoisomerase II inhibitor in human acute leukemia cells in vitro and in vivo. Blood. 110(6): 2034-2040.
Zhang W, et al. (2007) Gender-specific differences in expression in human lymphoblastoid cell lines. Pharmacogenet Genomics. 17(6): 447-450.
Zhang X, et al. (1999) Telomere shortening and apoptosis in telomerase-inhibited human tumor cells. Genes Dev. 13(18): 2388-2399.
Zijlmans JM, et al. (1997) Telomeres in the mouse have large inter-chromosomal variations in the No. of T2AG3 repeats. Proc Natl Acad Sci USA. 94(14): 7423-7428.
Communication pursuant to Rules 161(1) and 162 EPC issued Aug. 2, 2011 for European Patent Application No. 09804177.5, which claims priority to PCT/US2009/069243 filed Dec. 22, 2009 (Applicant—University of Utah Research Foundation // Inventor—R. Cawthon) (2 pages).
International Preliminary Report on Patentability issued Jun. 29, 2011 for PCT/US2009/069243 filed Dec. 22, 2009, later published as WO 2010/075413 as Jul. 1, 2010 (Applicant—University of Utah Research Foundation // Inventor—R. Cawthon) (6 pages).
International Search Report and Written Opinion issued Mar. 30, 2010 for PCT/US2009/069243 filed Dec. 22, 2009, later published as WO 2010/075413 as Jul. 1, 2010 (Applicant—University of Utah Research Foundation // Inventor—R. Cawthon) (15 pages).
Austriaco, Jr., et al., "Changes of telomere length cause reciprocal changes in the lifespan of mother cells in *Saccharomyces cerevisiae*," Proc. Natl. Acad. Sci. USA, 94:9768-9772 (1997).
Brummendorf, et al., "Telomere length in leukocyte subpopulations of patients with aplastic anemia," Blood, 97(4): 895-900 (2001).
Cherif, et al., "Ageing and telomeres: a study into organ- and gender-specific telomere shortening," Nuclein Acids Research, 31(5): 1576-1583 (2003).
Griffith, et al. (1999) "Mammalian telomeres end in a large duplex loop," Cell, 97:503-514.
Munoz-Jordan et al. (2001) "T-loops at trypanosome telomeres," EMBO J., 20: 579-588.
Samani, et al. "Telomere shortening in atherosclerosis," Lancet, 358:472-473 (2001).
Request for Continued Examination filed on Nov. 25, 2009 for U.S. Appl. No. 10/543,111, filed Mar. 10, 2006. (Applicant—University of Utah; Inventor—Cawthon et al.) (1 pages).
Non-Final Office Action issued May 2, 2013 for U.S. Appl. No. 10/543,111, filed Mar. 10, 2006. (Applicant—University of Utah; Inventor—Cawthon et al.) (7 pages).
Amendment and Response filed Nov. 1, 2013 for U.S. Appl. No. 10/543,111, filed Mar. 10, 2006. (Applicant—University of Utah; Inventor—Cawthon et al.) (6 pages).
Final Office Action issued Jan. 10, 2014 for U.S. Appl. No. 10/543,111, filed Mar. 10, 2006. (Applicant—University of Utah; Inventor—Cawthon et al.) (10 pages).
Response to Restriction Requirement filed Jun. 5, 2007 for U.S. Appl. No. 10/355,626, filed Jan. 31, 2003. (Applicant—University of Utah; Inventor—Cawthon et al.) (7 pages).
Restriction Requirement issued Aug. 9, 2006 for U.S. Appl. No. 10/355,626, filed Jan. 31, 2003. (Applicant—University of Utah; Inventor—Cawthon et al.) (8 pages).
Notice of Abandonment issued Mar. 6, 2007 for U.S. Appl. No. 10/355,626, filed Jan. 31, 2003. (Applicant—University of Utah; Inventor—Cawthon et al.) (2 pages).
Amendment After Final fiiled Oct. 7, 2008 for U.S. Appl. No. 10/355,626, filed Jan. 31, 2003. (Applicant—University of Utah; Inventor—Cawthon et al.) (1 pages).
Request for Continued Examination filed Dec. 19, 2008 for U.S. Appl. No. 10/355,626, filed Jan. 31, 2003. (Applicant—University of Utah; Inventor—Cawthon et al.) (11 pages).
Examiner Interview Summary issued Jul. 22, 2009 for U.S. Appl. No. 10/355,626, filed Jan. 31, 2003. (Applicant—University of Utah; Inventor—Cawthon et al.) (2 pages).
Issue Notification issued Mar. 24, 2010 for U.S. Appl. No. 10/355,626, filed Jan. 31, 2003. (Applicant—University of Utah; Inventor—Cawthon et al.) (1 pages).
Issue Notification issued Oct. 12, 2011 for U.S. Appl. No. 12/700,475, filed Feb. 4, 2010. (Applicant—University of Utah; Inventor—Cawthon et al.)(1 pages).
Requirement for Restriction/Election issued Jan. 24, 2013 for U.S. Appl. No. 13/028,910, filed Feb. 16, 2011 and published as 2011/0207128 on Aug. 25, 2011 (Applicant—University of Utah; Inventor—Cawthon et al.) (8 pages).
Notice of Abandonment issued Aug. 7, 2013 for U.S. Appl. No. 13/028,910, filed Feb. 16, 2011 and published as 2011/0207128 on Aug. 25, 2011 (Applicant—University of Utah; Inventor—Cawthon et al.) (8 pages).
Frenck et al. The rate of telomere sequence loss in human leukocytes varies with age. PNAS 95:5607-5610 (1998) (4 pages).
Non-Final Office Action issued on Jan. 8, 2015 by the USPTO for U.S. Appl. No. 10/543,111, filed Mar. 10, 2006 (Inventor—Cawthorn; Applicant University of Utah Research Foundation) (9 pages).
International Search Report and Written Opinion mailed on Oct. 28, 2015 by the International Searching Authority for International Patent Application No. PCT/US2015/036991, which was filed on Jun. 22, 2015 (Inventor—Harley et al.; Applicant—Telome Health, Inc.; (12 pages).
Brouilette, S.W. et al., Telomere Length, Risk of Coronary Heart Disease, and Stain Treatment in the West of Scotland Primary Prevention Study: A Nested Case-Control Study, Lancet, 369: 107-14 (2007).
Willeit, P. et al., Cellular Aging Reflected by Leukocyte Telomere Length Predicts Advanced Atherosclerosis and Cardiovascular Disease Risk, Aterioscler Thromb Vasc Biol, 30: 1649-56 (2010).

* cited by examiner

Cycle 1

Cycle 2

MONOCHROME MULTIPLEX QUANTITATIVE PCR

CROSS-REFERENCE TO RELATED PATENT APPLICATIONS

This application claims priority to U.S. Provisional Application No. 61/139,890, filed on Dec. 22, 2008, which is hereby incorporated herein by reference in its entirety.

STATEMENT REGARDING FEDERALLY FUNDED RESEARCH

Portions of the research and inventions disclosed herein may have been made with U.S. Government support under the National Institutes of Health Grant No. 5R21AG030034. The U.S. government has certain rights in this invention.

TECHNICAL FIELD

Disclosed are methods for determining the relative and absolute copy number of a first target nucleic acid sequence as compared to a second target nucleic acid sequence in a single reaction with a single detection label and kits useful in practicing the methods.

BACKGROUND OF THE INVENTION

Real-time quantitative polymerase chain reaction (QPCR) determines, for each reaction well, the $C_t$, i.e. the fractional cycle number at which the well's rising fluorescence (proportional to product formation) crosses a set threshold that is several standard deviations above the baseline fluorescence (Higuchi, R., Fockler, C., Dollinger, G. and Watson, R. (1993) Kinetic PCR analysis: real-time monitoring of DNA amplification reactions. *Biotechnology* (N Y), 11, 1026-1030). The $C_t$ versus log(amount of input target DNA) plot is linear, allowing relative quantitation of unknowns by comparison to a standard curve derived from amplifying, in the same plate, serial dilutions of a reference DNA sample.

For many QPCR applications, the investigator wishes to normalize the signal from a target sequence (T) to the signal from a reference sequence (R). Early studies measured T and R in separate (monoplex) reactions with a dye that fluoresces upon intercalation into any double-stranded DNA, e.g. ethidium bromide or SYBR Green I, and this approach continues. More recent studies have measured T and R in the same reaction vessel, in a multicolor multiplex QPCR, using separate fluorescent dyes with distinct excitation/emission spectra for each of the DNA sequences being quantified (Wittwer, C. T., Herrmann, M. G., Gundry, C. N. and Elenitoba-Johnson, K. S. (2001) Real-time multiplex PCR assays. Methods, 25, 430-442). Measurement of T/R ratios by multiplex QPCR cuts in half the number of separate PCR reactions that must be run. Furthermore, since both T and R signals are collected within each reaction vessel, variation in the amount of a given DNA sample that is pipetted for replicate reactions no longer generates variation in the T/R ratios, as it does when T and R are measured in separate wells in monoplex QPCR.

The main disadvantage of multicolor multiplex QPCR is the relatively high cost of the fluorescent probes, and the high cost of the specialized QPCR machines that are equipped to read two or more fluorescent colors. In traditional approaches to multiplex PCR (whether or not the PCR is quantitative), it is also sometimes excessively time-consuming to identify primer sets and primer concentrations that prevent the earlier amplification of a higher copy number template by one primer pair from inhibiting the later amplification of a different, lower copy number template by a second primer pair

SUMMARY OF THE INVENTION

The present invention provides methods of determining the copy number of two or more target nucleic acid sequences in a single reaction with a single detection label. Also disclosed are methods for determining the copy number of telomeric sequences. This data may be used for associating the measured telomere length with a mortality risk or likelihood of disease occurrence that corresponds to a telomere length observed in a population.

Disclosed herein are methods and compositions for determining the copy number of a first target nucleic acid as compared to the copy number of a second target nucleic acid by a monochrome multiplex quantitative PCR (MMQPCR) in a single well, a homogenous system, with a single detection label.

Additional advantages of the disclosed methods and compositions will be set forth in part in the description which follows, and in part will be understood from the description, or can be learned by practice of the disclosed methods and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE FIGURES

The accompanying drawings, which are incorporated in and constitute a part of this specification, illustrate several embodiments of the disclosed methods and compositions and together with the description, serve to explain the principles of the disclosed method and compositions.

DETAILED DESCRIPTION

Figure 1:
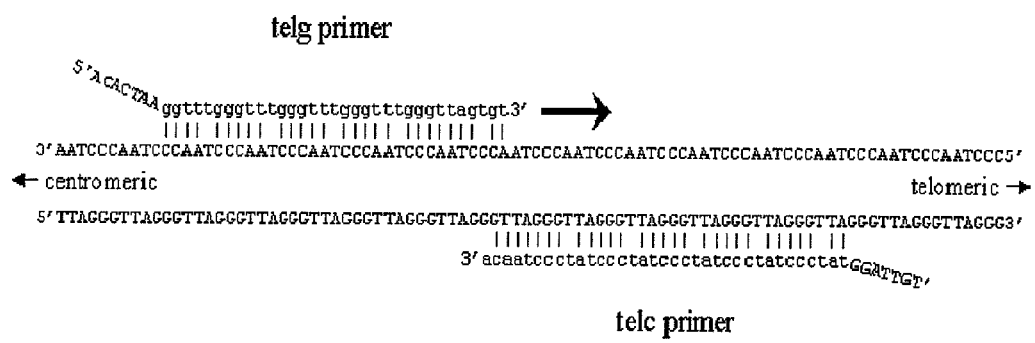
FIG. 1 shows in Cycle 1 the telg primer hybridizes to native telomere sequences and primes DNA synthesis. The telc primer hybridizes native telomere sequences but cannot prime DNA synthesis, due to its 3' terminal mismatch. When hybridized to each other as shown, and in other configurations not shown, telg and telc have multiple mismatches, including at their 3' terminal bases, so primer dimer formation is inhibited. The 3' ends of telg and telc can align as a perfectly complementary three by overlap, it is not stable enough to allow efficient primer dimer formation. In Cycle 2, telc can hybridize along telg primer extension products that were synthesized in Cycle 1, but can only prime DNA synthesis when hybridized in the configuration shown, since other configurations produce a mismatch at telc's 3' terminal base. In the telg extension product, the overbar marks the sequence of the telg primer itself, and the italicized bases mark sequence newly synthesized in Cycle 1 of the PCR. The non-templated capitalized sequences at the 5' ends of the primers prevent the 3' ends of the telomere PCR product from priming DNA synthesis in the middle of other copies of the telomere PCR product.
Figure 1:
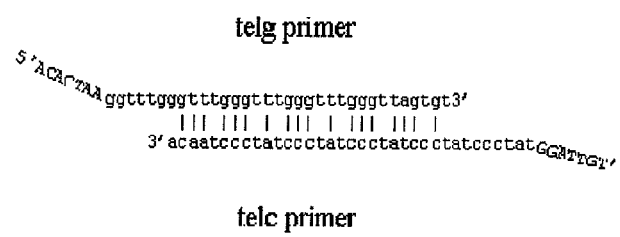
Figure 1:
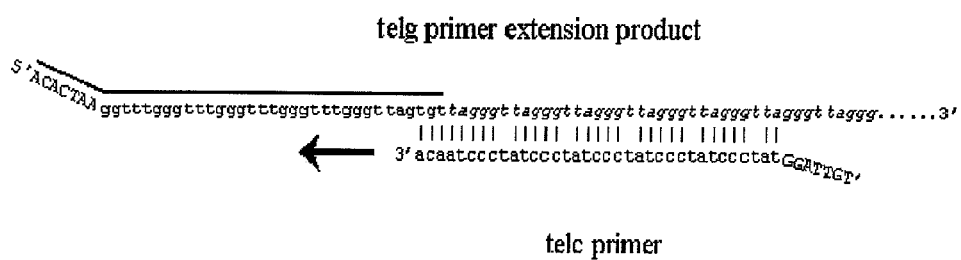

The present invention comprises methods and systems directed at determining the copy number of one or more target nucleic acids. The disclosed method and compositions can be understood more readily by reference to the following detailed description of particular embodiments and the Example included therein and to the Figures and their previous and following description.

The disclosed compositions and methods can be used for real-time detection of target nucleic acids. Real-time detection is detection can take place during or immediately after the amplification reaction or operation. Generally, such detection can be accomplished by detecting amplification product at one or more discrete times during amplification, continuously during all or one or more portions of the amplification, or a combination of discrete times and continuous detection. Real-time detection can be aided by the use of labels or moieties that embody or produce a detectable signal that can be detected without disrupting the amplification reaction or operation. Fluorescent labels are an example of useful labels for real-time detection. A particularly useful means of obtaining real-time detection is the use of detection labels in the amplification operation. With suitably designed detection labels, detection signals, including fluorescent signals, can be generated as amplification proceeds. In most such cases, the detection signals will be in proportion to the amount of amplification product and/or amount of target sequence or target molecule.

Disclosed herein are methods for determining the copy number of a first target nucleic acid and a second target nucleic acid. A target nucleic acid can be obtained from a sample or artificially generated as described elsewhere herein.

All patents, patent applications and publications cited herein, whether supra or infra, are hereby incorporated by reference in their entireties into this application in order to more fully describe the state of the art as known to those skilled therein as of the date of the invention described and claimed herein.

It is to be understood that this invention is not limited to specific synthetic methods, or to specific recombinant biotechnology methods unless otherwise specified, or to particular reagents unless otherwise specified, to specific pharmaceutical carriers, or to particular pharmaceutical formulations or administration regimens, as such may, of course, vary.

DEFINITIONS AND NOMENCLATURE

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like. Reference to "a component" can include a single or multiple components or a mixtures of components unless the context clearly dictates otherwise.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "specifically binds" is meant that the composition recognizes and physically interacts with its cognate target. For example, a primer can specifically bind to its target nucleic acid. For example, a primer of the first primer set can specifically bind to the first target nucleic acid sequence and does not significantly recognize and interact with other targets or target nucleic acid sequences.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for target nucleic acids (for example, genes and/or mRNAs) have at least 80%-90% sequence complementarity, at least 91%-95% sequence complementarity, at least 96%-99% sequence complementarity, or at least 100% sequence complementarity to the region of the target to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: the described monochrome multiplex quantitative PCR (MMQPCR) described herein as well as nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "primer set" is meant to mean at least two primers that each contain a complementary sequence to an opposite strand of the same target sequence. In a primer set, at least one of the two primers must be a "forward primer" at least one of the two primers must be a "reverse primer". A "forward primer" is a primer that is complementary to a sense strand of a target nucleic acid, wherein a "reverse primer" is a primer that is complementary to the complement of the sense strand of the target nucleic acid (also referred to as the anti-sense strand of the target nucleic acid). A primer set can be a pair of primers capable of being used in a PCR reaction.

By "amplicon" is meant to mean pieces of DNA formed as the products of natural or artificial amplification events. For example, they can be formed via the methods described herein, polymerase chain reactions (PCR) or ligase chain reactions (LCR), as well as by natural gene duplication.

By "specifically hybridizes" is meant that a probe, primer, or oligonucleotide recognizes and physically interacts (that is, base-pairs) with a substantially complementary nucleic acid (for example, a target nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Target Samples

Target samples can be derived from any source that has, or is suspected of having, target molecules. Target samples can contain, for example, a target molecule(s) such as nucleic acids. A target sample can be the source of target nucleic acids. A target sample can include natural target nucleic acids, chemically synthesized target nucleic acids, or both. A target sample can be, for example, a sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful target samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

1. Target Nucleic Acids

Nucleic acid samples can be derived from any source that has, or is suspected of having, target nucleic acids. A nucleic acid sample is the source of nucleic acid molecules and nucleic acid sequences such as target nucleic acids. The nucleic acid sample can contain RNA or DNA or both. The target nucleic acid can also be cDNA. In addition, mRNA can be reverse transcribed to form cDNA which can then serve as a target nucleic acid for use in the methods described herein.

A "target nucleic acid" or "target sequence" is meant a nucleic acid sequence on a double or single stranded nucleic acid. By "nucleic acid" or "oligonucleotide" or grammatical equivalents herein is meant at least two nucleotides covalently linked together. A nucleic acid of the present invention will generally contain phosphodiester bonds, although in some cases, nucleic acid analogs are included that may have alternate backbones, comprising, for example, phosphoramide (Beaucage, S. L. et al., Tetrahedron 49: 1925-63 (1993), and references therein; Letsinger, R. L. et al., J. Org. Chem. 35: 3800-03 (1970); Sprinzl, M. et al., Eur. J. Biochem. 81: 579-89 (1977); Letsinger, R. L. et al., Nucleic Acids Res. 14:3487-99 (1986); Sawai et al, Chem. Lett. 805 (1984); Letsinger, R. L. et al., J. Am. Chem. Soc. 110: 4470 (1988); and Pauwels et al., Chemica Scripta 26:141-49 (1986)), phosphorothioate (Mag, M. et al., Nucleic Acids Res. 19:1437-41 (1991); and U.S. Pat. No. 5,644,048), phosphorodithioate (Briu et al., J. Am. Chem. Soc. 111:2321 (1989)), O-methylphosphoroamidite linkages (see Eckstein, Oligonucleotides and Analogues: A Practical Approach, Oxford University Press, 1991), and peptide nucleic acid backbones and linkages (Egholm, M., Am. Chem. Soc. 114:1895-97 (1992); Meier et al., Chem. Int. Ed. Engl. 31:1008 (1992); Egholm, M., Nature 365: 566-68 (1993); Carlsson, C. et al., Nature 380: 207 (1996), all of which are incorporated by reference). Other analog nucleic acids include those with positive backbones (Dempcy, R. O. et al., Proc. Natl. Acad. Sci. USA 92:6097-101 (1995)); non-ionic backbones (U.S. Pat. Nos. 5,386,023; 5,637,684; 5,602,240; 5,216,141; and 4,469,863; Kiedrowshi et al., Angew. Chem. Intl. Ed. English 30:423 (1991); Letsinger, R. L. et al., J. Am. Chem. Soc. 110: 4470 (1988); Letsinger, R. L. et al., Nucleoside & Nucleotide 13: 1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4: 395 (1994); Jeffs et al., J. Biomolecular NMR 34:17 (1994)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. 169-176 (1995)); all references are hereby expressly incorporated by reference.

Any nucleic acid sequence sought to be measured, identified, detected or whose copy number is sought to be determined can serve as a target nucleic acid sequence. In the methods described herein, there can be more than one target nucleic acid sequence. In the event that two target nucleic acid sequences are present, they will be referred to as a first and second target nucleic acid sequence, respectfully. In the event that three target nucleic acid sequences are present, they will be referred to as a first, a second and a third target nucleic acid sequence, respectfully and so on. The target nucleic acids described in the methods herein can have the same, similar or different copy numbers. For example, the first target nucleic acid is a nucleic acid sequence of multiple copy numbers and the second target nucleic acid is a single copy gene. For example, the first target nucleic acid can be telomeric repeat sequences, mtDNA, rDNA or Alu repeat DNA. For example, the first target nucleic acid can be cDNA reverse-transcribed from a high copy number mRNA, and the second target nucleic acid can be cDNA reverse-transcribed from a low copy number mRNA.

Single copy genes are genes that have a single copy per haploid genome. Single copy genes therefore have two copies per cell. Single copy genes include, but are not limited to, the albumin gene or the beta-globin gene.

Telomeres are specialized structures found at the ends of linear chromosomes of eukaryotes. Telomeres are generally composed of short tandem repeats, with a repeat sequence unit specified by the telomerase enzyme particular to that organism. Telomere repeat sequences are known for a variety of organisms. For vertebrates, plants, certain types of molds, and some protozoans, the sequences are perfect repeats. For example, the human repeat sequence unit is (TTAGGG)n. (SEQ ID NO:1) In other organisms, the repeats sequences are irregular, such as those of *Sacharomyces cerevisiae* where the sequence is variable G1-3 T/C1-3A. In some eukaryotic organisms, telomeres lack the short tandem sequence repeats but have sequence elements that function as telomeres. For example, in the fruit fly *Drosophila melanogaster*, the telomere is a composite of retrotransposon elements HeT-A and TART while in the mosquito *Anopheles gambiae* the telomeres are arrays of complex sequence tandem repeats. For the purposes of the present invention, telomeres of different structures are encompassed within the scope of the present invention.

In addition to the repeat sequences, the 3' end of some telomeres contains a single stranded region, which for humans is located on the G rich strand. The single strand is composed of $(TTAGGG)_n$. (SEQ ID NO:1) repeats, with n being generally about 9-35, although it can be less or more. As used herein, the length of the 3' single stranded region can also be correlated with mortality risk.

Typically, the DNA replicative machinery acts in the 5' to 3' direction, and synthesis of the lagging strand occurs discontinuously by use of short RNA primers that are degraded following strand synthesis. Since sequences at the 3' end of a linear DNA are not available to complete synthesis of the region previously occupied by the RNA primer, the terminal 3' region of the linear chromosome is not replicated. This "end replication problem" is solved by the action of telomerase, a telomere specific ribonucleoprotein reverse transcriptase. The telomerase enzyme has an integral RNA component that acts as a template for extending the 3' end of the telomere. Repeated extensions by telomerase activity results in the generation of telomere repeats copied from the telomerase-bound RNA template. Following elongation by telomerase, lagging strand synthesis by DNA polymerase completes formation of the double stranded telomeric structure.

In normal human somatic cells, telomerase is not expressed or expressed at low levels. Consequently, telomeres shorten by 50-200 bp with each cell division until the cells reach replicative senescence, at which point the cells lose the capacity to proliferate. This limited capacity of cells to replicate is generally referred to as the Hayflick limit, and may provide cells with a counting mechanism, i.e., a mitotic clock, to count cell divisions and regulate cellular development. Correspondingly, activation of telomerase in cells lacking telomerase activity, for example by expressing telomerase from a constitute retroviral promoter or activation of endogenous polymerase, allows the cells to maintain proliferative capacity and leads to immortalization of the cell.

Interestingly, these immortalized cells have short stable telomeres while the shortest telomeres become extended. This phenomena suggests that telomerase enzyme protects short telomeres from further shortening while extending those that have fallen below a certain threshold length. Thus, presence of telomerase activity does not appear to be necessary when telomeres are a certain length, but becomes critical to maintenance of telomere integrity when the length falls below a critical limit.

It is well established that the length and integrity of telomeres is important for proper segregation of chromosomes and cell growth. For example, development of many types of cancers correlates with activation of telomere maintenance while cell senescence correlates with loss of telomere integrity. Shortening of telomere induced by inhibiting telomerase activity can lead to proliferative senescence and cell apoptosis (Zhang, X. et al., Genes Dev. 2388-99 (1999)). Moreover, genetic knockouts of telomerase RNA in mice results in animals with developmental defects, age related pathologies, and increased cancer susceptibility (Rudolph, K. L. et al., Cell 96: 701-12 (1999); Herrera, E. et al., EMBO J. 18: 2950-60 (1999)). Similarly, in the autosomal dominant disorder of dyskeratosis congenital (DKC), which arises from a mutation in the gene encoding the RNA component of telomerase, afflicted patients display accelerated telomere shortening and die at a median age of 16 years (maximum approximately 50 years), usually from severe infections secondary to bone marrow failure. Clinical features of DKC patients, further suggestive of accelerated aging, include premature graying and loss of hair; skin dyspigmentation; poor wound healing; high risk of severe infections; and an increased incidence of malignancies, osteoporosis, and pulmonary fibrosis. In addition, the shortest average telomere lengths measured in blood DNA from normal elderly individuals overlap with the highest average telomere lengths measured in blood from DKC patients.

In view of the role telomeres play in cell growth and cell senescence, it is desirable to have methods of predicting the occurrence of age related diseases and mortality risk based on length of telomeres. The methods described herein, including the MMQPCR methods, will provide a basis for identifying individuals with increased risk of developing particular age-associated diseases, such as cancer and hypertension, such that early medical intervention can be administered to individuals in high risk groups.

In the methods described herein, the copy number of a telomere may be determined for a single chromosome in a cell. In an aspect, the average copy number of a telomere or mean telomere copy number is measured for a single cell. In another embodiment, the average copy number of a telomere or mean telomere copy number is measured for a population of cells. A change in telomere copy number is an increase or decrease in telomere copy number, in particular an increase or decrease in the average telomere copy number. The change may be relative to a particular time point, i.e., telomere copy number of an organism at time t1 as compared to telomere length at some later time t2. A change or difference in telomere copy number may also be compared as against the average or mean telomere copy number of a particular cell population or organism population. In some aspects, a change or difference in telomere copy number may also be compared as against the average or mean telomere copy number of a population not suffering from a disease condition. In certain embodiments, change in telomere copy number is measured against a population existing at different time periods.

Although, telomere copy number may be determined for all eukaryotes, in a one aspect, telomere copy numbers are determined for vertebrates, including without limitation, amphibians, birds, and mammals, for example rodents, ungulates, and primates, particularly humans. Telomere copy numbers can also be determined for organisms in which longevity is a desirable trait or where longevity and susceptibility to disease are correlated. In another aspect, the telomeres may be measured for cloned organisms in order to assess the mortality risk or disease susceptibility associated with altered telomere integrity in these organisms.

Telomeric nucleic acid sequences, such as those described above can serve as a target sequence. Telomeric nucleic acid sequences, or any other target nucleic acid, may be any length, with the understanding that longer sequences are more specific. In some embodiments, it may be desirable to fragment or cleave the sample nucleic acid into fragments of 100-10,000 base pairs. In one aspect, fragments of roughly 500 basepairs can be used. Fragmentation or cleavage may be done in any number of ways well known to those skilled in the art, including mechanical, chemical, and enzymatic methods. Thus, the nucleic acids may be subjected to sonication, French press, shearing, or treated with nucleases (e.g., DNase, restriction enzymes, RNase etc.), or chemical cleavage agents (e.g., acid/piperidine, hydrazine/piperidine, iron-EDTA complexes, 1,10-phenanthroline-copper complexes, etc.).

2. Polymerases

In the methods described herein, an amplification enzyme is required. For example, following contacting the primers to the target nucleic acids, the reaction can be treated with an amplification enzyme. Amplification enzymes are generally polymerases, such as DNA polymerases. A variety of suitable polymerases are well known in the art, including, but not limited to, Taq DNA polymerase, KlenTaq, Tfl polymerase, DynaZyme, etc. Generally, all polymerases are applicable to the present invention. In one aspect, polymerases are thermostable polymerases lacking 3' to 5' exonuclease activity, or polymerases engineered to have reduced or non-functional 3' to 5' exonuclease activities (e.g., Pfu(exo-), Vent(exo-), Pyra(exo-), etc.), since use of polymerases with strong 3' to 5' exonuclease activity tends to remove the mismatched 3' terminal nucleotides that are needed in some applications to prevent or delay primer dimer amplifications, and in other applications to carry out allele-specific amplifications. Also applicable are mixtures of polymerases used to optimally extend hybridized primers. In another aspect, polymerase enzymes useful for the present invention are formulated to become active only at temperatures suitable for amplification.

Presence of polymerase inhibiting antibodies, which become inactivated at amplification temperatures, or sequestering the enzymes in a form rendering it unavailable until amplification temperatures are reached, are all suitable. These polymerase formulations allow mixing all components in a single reaction vessel while preventing priming of non-target nucleic acid sequences.

In addition, those skilled in the art will appreciate that various agents may be added to the reaction to increase processivity of the polymerase, stabilize the polymerase from inactivation, decrease non-specific hybridization of the primers, or increase efficiency of replication. Such additives include, but are not limited to, dimethyl sulfoxide, formamide, acetamide, glycerol, polyethylene glycol, or proteinacious agents such as *E. coli.* single stranded DNA binding protein, T4 gene 32 protein, bovine serum albumin, gelatin, etc. In another aspect, the person skilled in the art can use various nucleotide analogs for amplification of particular types of sequences, for example GC rich or repeating sequences. These analogs include, among others, c7-dGTP, hydroxymethyl-dUTP, dITP, 7-deaza-dGTP, etc.

3. Primers

By "primer", "primer nucleic acid", "oligonucleotide primer", "oligonucleotide probe" or grammatical equivalents as used herein is meant a nucleic acid that will hybridize to some portion of a target nucleic acid. The primers or probes of the present invention are designed to be substantially complementary to a target sequence such that hybridization of the target sequence and the primers of the present invention occurs.

In some aspects, a primer can be designed to block the primer from priming extension of the target nucleic acid in all but one configuration. For example, one of the primers in a primer set can be designed to block the primer from priming the extension of the target nucleic acid by creating a mismatched base at the 3' end of the primer. By designing and utilizing such a primer, the primer is still able to hybridize to its complementary sequence; however, it will only prime DNA synthesis is a single confirmation, thus giving predictability to the amplicon size and therefore predictability to the Tm of the amplicon.

For example, disclosed herein are primers and primer sets, wherein one primer of the first primer set comprises at least one nucleotide adjacent to the 3' end of the primer, wherein said nucleotide is mismatched against, not complementary to, the target nucleic acid, but complementary to the 3' terminal nucleotide of the other primer in the primer set.

Also disclosed herein are primers and primer sets, wherein one primer of a primer set comprises at least one nucleotide adjacent to the 3' end of the primer, wherein said nucleotide is mismatched against, not complementary to, the target nucleic acid, but complementary to the 3' terminal nucleotide of the other primer in the primer set, wherein the extension product of the mismatch-containing primer of the primer set can be hybridized by the other primer in the primer set, allowing said other primer to prime DNA synthesis along said extension product.

To ensure that a blocked primer will only prime in a single, specific configuration, a primer set including the blocked primer can be designed such that the primers of the primer set overlap with perfect complementarity over the region of the mismatched base present in the blocked primer. Such a design can be performed so as to prevent primer dimer formation and to minimize the ability of the two primers to prime each other. Such a design can be utilized when the target nucleic acid sequence is a sequence comprising multiple repeats such as the repeats found in a telomere (telomeric sequence). An example of such a method is described elsewhere herein, including the Examples below.

As described herein, the primers for direct amplification of telomere repeats can comprise a first primer which hybridizes to a first single strand of the target nucleic acid and a second primer which hybridizes to a second single strand of the target nucleic acid, where the first and second strands are substantially complementary. The primers are capable of primer extension by polymerase when hybridized to their respective strands. That is, the primers hybridized to the target nucleic acid have their 3' terminal nucleotide residues complementary to the nucleotide residue on the target nucleic acid such that the primers are extendable by polymerase. Selected primers are complementary to repetitive units of the repetitive region. For example, at least one nucleotide residue of at least one of the primers can be altered to produce mismatches with a nucleotide residue of at least one repetitive unit to which the primer hybridizes, wherein the altered nucleotide residue also produces a mismatch with the 3' terminal nucleotide residue of the other primer when the primers hybridize to each other. The inclusion of a mismatch prevents or limits primer extension and primer-primer hybrids.

A primer set for direct amplification of telomere repeats can comprise a primer set wherein at least one nucleotide residue of the first primer is altered to produce a mismatch between the altered residue and a nucleotide residue of at least one repetitive unit of the first strand to which the primer hybridizes, wherein the altered nucleotide residue also produces a mismatch with the 3' terminal nucleotide residue of the second primer when the first and second primers hybridize to each other. The altered nucleotide residue can be one or more nucleotide residues from the 3' terminal nucleotide to allow efficient extension by polymerase when the altered primer hybridizes to target nucleic acids. For example, the altered nucleotide residue can be at least 1 nucleotide residue, at least 2 nucleotide residues, or at least 3 nucleotide residues from the 3' terminal nucleotide to allow efficient extension by polymerase when the altered primer hybridizes to target nucleic acids.

As discussed elsewhere herein, the primers of the primer sets can be designed to have similar Tms to limit generation of undesirable amplification products and to permit amplification and detection of several target nucleic acids in a single reaction volume. In addition, since the telomeres of various organisms have differing repetitive unit sequences, amplifying telomeres of a specific organism will employ primers specific to the repetitive unit of each different organism. Human telomeric sequences are used herein to illustrate practice of the present invention for direct amplification and quantitation of tandemly repeated nucleic acid sequences, but the invention is not limited to the disclosed specific embodiment.

Also disclosed are primers to increase the melting temperature (Tm) of the resultant amplicon above that of the other amplicon of the methods described herein. These primers can be referred to as primers comprising a "GC-clamp". "GC-clamps" typically refers to the presence of G or C bases within the last five bases from the 3' end of primers that helps promote specific binding at the 3' end due to the stronger bonding of G and C bases. Typically, more than 3 G's or C's should be avoided in the last 5 bases at the 3' end of the primer. However, in the methods described herein primers comprising a "GC-clamp" are primers that comprise a 5' tag sequence (GC-clamp) that confers a higher melting temperature on the resulting PCR product (amplicon) than the melting temperature without the GC-clamp. The 5' tag sequence of primers comprising a "GC-clamp" comprise a GC-clamp on the 5' end of the primer sequence that is not complementary to any part of the target nucleic acid sequence. A "GC-clamp" is a series of G and C nucleotides that can be linked to the 5' end of a primer in order to increase the melting temperature of the amplicon. A GC-clamp can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides long. A GC-clamp can also be referred to a GC-rich region or GC-rich tag.

GC-clamps can be used in the methods described herein to increase the Tm of one of the amplicons. By increasing the Tm of the amplicon, a fluorescent signal can be acquired at a temperature high enough to completely melt the other amplicon, thus allowing for the acquisition of a fluorescent signal for two or more different amplicons at two or more different temperatures. GC-clamped primers can be designed for use in the same amplification reaction such that the GC-clamps on different primers are different from one another so as to prevent hairpin formation or primer dimers that could result in a cessation of the amplification reaction.

Since primers hybridized to target nucleic acids must be capable of primer extension, alterations of the first and second primers must be on non-complementary nucleotides of the repetitive unit. Thus, in one aspect, when both the first and second primers comprise altered residues, the alterations are at nucleotide positions adjacent to the repetitive unit. In another aspect, the alterations are situated on nucleotide positions non-adjacent to the repetitive unit. In general, mismatches at adjacent nucleotide positions provide for the most number of base paired or complementary residues between the altered nucleotide and the 3' terminal nucleotide, which may be important for efficiently amplifying short repetitive sequences (i.e., 3-6 basepairs).

Complementarity of the primers to the target nucleic acid need not be perfect. Thus, by "complementary" or "substantially complementary" herein is meant that the probes are sufficiently complementary to the target sequences to hybridize under normal reaction conditions. Deviations from perfect complementary are permissible so long as deviations are not sufficient to completely preclude hybridization. However, if the number of alterations or mutations is sufficient such that no hybridization can occur under the least stringent of hybridization conditions, as defined below, the sequence is not a complementary target sequence.

Although primers are generally single stranded, the nucleic acids as described herein may be single stranded or double stranded, as specified, or contain portions of both double stranded or single stranded sequence. The nucleic acid may be DNA, RNA, or hybrid, where the nucleic acid contains any combination of deoxyribo- and ribonucleotides, and any combination of bases, including uracil, adenine, thymine, cytosine, guanine, xanthine hypoxanthine, isocytosine, isoguanine, inosine, etc. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred herein as a nucleotide.

The size of the primer nucleic acid may vary, as will be appreciated by those in the art, in general varying from 5 to 500 nucleotides in length. For example, with primers of between 10 and 100 nucleotides, between 12 and 75 nucleotides, and from 15 to 50 nucleotides can be used, depending on the use, required specificity, and the amplification technique.

For any primer pair, the ability of the primers to hybridize to each other may be examined by aligning the sequence of the first primer to the second primer. The stability of the hybrids, especially the thermal melting temperature (Tm), may be determined by the methods described below and by methods well known in the art. These include, but are not limited to, nearest-neighbor thermodynamic calculations (Breslauer, T. et al., Proc. Natl. Acad. Sci. USA 83:8893-97 (1986); Wetmur, J. G., Crit. Rev. Biochem. Mol. Biol. 26:227-59 (1991); Rychlik, W. et al., J. NIH Res. 6:78 (1994)), Wallace Rule estimations (Suggs, S. V. et al "Use of Synthetic oligodeoxyribonucleotides for the isolation of specific cloned DNA sequences," Developmental biology using purified genes, D. B. Brown, ed., pp 683-693, Academic Press, New York (1981), and Tm estimations based on Bolton and McCarthy (see Baldino, F. J. et al., Methods Enzymol. 168: 761-77 (1989); Sambrook, J. et al., Molecular Cloning: A Laboratory Manual, Chapter 10, Cold Spring Harbor Laboratory Press, Cold Spring Harbor, N.Y., (2001)). All references are hereby expressly incorporated by reference. The effect of various parameters, including, but not limited to, ionic strength, probe length, G/C content, and mismatches are taken into consideration when assessing hybrid stability. Consideration of these factors are well known to those skilled in the art (see, e.g., Sambrook, J., supra).

The primers that can be used in the methods described herein can be used to amplify various target nucleic acids. A single primer set, for example a primer pair, may be used to amplify a single target nucleic acid. In another embodiment, multiple primer sets may be used to amplify a plurality of target nucleic acids. Amplifications may be conducted separately for each unique primer set, or in a single reaction vessel using combinations of primer sets, generally known in the art as multiplexing. When multiple primer sets are used in a single reaction, primers are designed to limit formation of undesirable products and limit interference between primers of each primer set.

The general PCR amplification reactions can be carried out according to procedures well known in the art, as discussed above (see, e.g., U.S. Pat. Nos. 4,683,195 and 4,683,202). The time and temperature of the primer extension step will depend on the polymerase, length of target nucleic acid being amplified, and primer sequence employed for the amplification. The number of reiterative steps required to sufficiently amplify the target nucleic acid will depend on the efficiency of amplification for each cycle and the starting copy number of the target nucleic acid. As is well known in the art, these parameters can be adjusted by the skilled artisan to effectuate a desired level of amplification. Those skilled in the art will understand that the present invention is not limited by variations in times, temperatures, buffer conditions, and the amplification cycles applied in the amplification process.

In hybridizing the primers to the target nucleic acids and in the disclosed amplification reactions, the assays are generally done under stringency conditions that allow formation of the hybrids in the presence of target nucleic acid. Those skilled in the art can alter the parameters of temperature, salt concentration, pH, organic solvent, chaotropic agents, or other variables to control the stringency of hybridization and also minimize hybridization of primers to non-specific targets (i.e., by use of "hot start" PCR or "touchdown" PCR).

4. Detection Labels

To aid in determining the copy number of target nucleic acids using the disclosed compositions and methods, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. In the methods described herein, a single detection label can be used. By a "single detection label" is meant to mean a single type of detection label. For example, a single detection label can be any detection label as described herein, however only one type of detection label can be used in each homogenous system. For example, a single detection label can be SYBR Green I (Invitrogen), fluorescein isothiocyanate (FITC), 5,6-carboxymethyl fluorescein, or Texas red but not a combination of all of these. Thus, SYBR Green I (Invitrogen), fluorescein isothiocyanate (FITC), 5,6-carboxymethyl fluorescein, or Texas red are each single detection labels, for example, SYBR Green I (Invitrogen) is a single detection label, fluorescein isothiocyanate (FITC) is a single detection label, 5,6-carboxymethyl fluorescein is a single detection label, and Texas red is a single detection label.

Another example is provided in the Examples below where SYBR Green is the "single detection label" used to determine the copy number of two different targets. In addition, a single detection label can also be referred to as a single, monochrome, detection label. A "single, monochrome detection label" is a single detection label that has only one color. For example, a single, monochrome detection label can be a detection label that emits a single color that can be detected.

Many such labels for incorporation into nucleic acids or coupling to nucleic acid probes are known to those of skill in the art. Examples of detection labels suitable for use in the disclosed method are radioactive isotopes, phosphorescent molecules, enzymes, antibodies, and ligands as well as fluorescent molecules including fluorescent dyes and fluorescent labels. Fluorescent labels are useful for real-time detection of amplification.

For example, the methods described herein can use fluorescent dyes that preferentially bind to double stranded nucleic acid amplification products during the PCR reaction, thereby providing continuous monitoring of product synthesis (see Higuchi, R. et al., Biotechnology 11: 1026-1030 (1993); Morrison, T. B. et al., Biotechniques 24: 954-962 (1998)).

Examples of suitable fluorescent labels include, but are not limited to, SYBR Green I (Invitrogen), fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethaneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.Fluorescent labels can be obtained from a variety of commercial sources, including Invitrogen, Carlsbad, Calif.; Amersham Pharmacia Biotech, Piscataway, N.J.; Molecular Probes, Eugene, Oreg.; and Research Organics, Cleveland, Ohio.

5. Instruments

Instrumentation suitable for use with the disclosed methods and compositions include but are not limited to ABI Prism 7700, Applied Biosystems Division, Perkin Elmer, Fosters City, Calif., USA; LightCycler™, Roche Molecular Biochemicals, Indianapolis, Ind., USA.

Various algorithms can be used to calculate the copy number of the target nucleic acids in the samples as described herein (see ABI Prism 7700 Software Version 1.7; Lightcycler™ Software Version 3; incorporated by reference). Determining copy number may involve use of standard samples with known copy number of the target nucleic acid and generation of standard curves from the logarithms of the standards and the cycle of threshold (Ct). In general, Ct is the PCR cycle or fractional PCR cycle where the fluorescence generated by the amplification product is several deviations above the baseline fluorescence (Higuchi, R. et al., supra). MMQPCR provides a linearity of about 7 to 8 orders of magnitude, which allows measurement of copy number of target nucleic acids over a wide dynamic range. The absolute number of target nucleic acid copies can be derived from comparing the Ct values of the standard curve and the samples.

The copy number of target nucleic acids may also be determined by comparative MMQPCR. Use of nucleic acids of known copy number or consistent copy number allows quantitating the copy number of target nucleic acids in a sample. The standard may be a single copy gene, a nucleic acid of known copy number, or when quantitating DNA copy number, a constitutively expressed housekeeping gene (see Johnson, M. R. Anal. Biochem. 278: 175-184 (2000); Boulay, J.-L., et al., Biotechniques 27: 228-232 (1999)).

Methods

Disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

A polymerase chain reaction (PCR) is a technique to amplify (i.e. increase the copy number of) one or more copies of a target nucleic acid sequence. The amplification can be across several orders of magnitude, generating thousands to billions of copies of a particular DNA sequence. The polymerase chain reaction relies on thermal cycling, consisting of cycles of repeated heating and cooling of the reaction to achieve DNA melting and enzymatic replication of the nucleic acid. As PCR progresses, the DNA generated is itself used as a template for replication, setting in motion a chain reaction in which the DNA template is exponentially amplified.

The PCR usually consists of a series of repeated temperature changes called cycles; each cycle typically consists of 2-3 discrete temperature steps. PCR can be carried out with cycles that have three or four steps, each at a different temperature. The cycling is often preceded by a single high temperature (>90° C.) step called a hold, which is applied in order to fully melt (i.e. render single-stranded) a double-stranded target nucleic acid sequence, followed by a repeated set of temperature changes during which amplification of the target nucleic acid occurs, followed by a final hold at the end for final product extension or brief storage.

The temperatures used and the length of time they are applied in each cycle depend on a variety of parameters. These include the enzyme used for DNA synthesis (e.g. the DNA polymerase), the concentration of divalent ions and dNTPs in the reaction, the melting temperature of the primers, and the melting temperatures of the products of amplification.

PCR includes at least a denaturation step, an annealing step and an elongation step. The elongation step can also be referred to as an extension step. In PCR the denaturing, annealing, and elongation steps occur, in order, at least once (a.k.a a single "cycle"), but are typically repeated for up to 40 cycles. When the DNA polymerase used requires heat activation, an additional step, called the initialization step, precedes the cycling stage of the PCR. Each step has a respective temperature associated with it. The temperature associated with each step is referred to as an initialization temperature, a denaturation temperature, an annealing temperature, and an extension or elongation temperature, respectively.

An initialization step can consist of heating the reaction to an initialization temperature of 90, 91, 92, 93, 94, 95, 96, 97, or 98° C., which can be held for 1, 2, 3, 4, 5, 6, 7, 8, 9, 10, 11, 12, 13, 14 or 15 minutes. The initialization step is typically only required when the DNA polymerases being used in the PCR requires heat activation. For example, if a thermostable polymerase is being used, an Initialization step with an initialization temperature of 98° C. can be used.

A denaturation step is typically the first step in the repeating cycle of the PCR and consists of heating the reaction to a denaturation temperature of 90, 91, 92, 93, 94, 95, 96, 97, or 98° C. for 15 16, 17, 18, 19, 20, 21, 22, 23, 24, 25, 26, 27, 28, 29, 30, 31, 32, 33, 34, or 35 seconds. The denaturation step melts the DNA template by disrupting the hydrogen bonds between complementary bases, yielding single strands of DNA.

An annealing step is typically the second step in the repeating cycle of the PCR and consists of lowering the temperature to an annealing temperature of 45, 46, 47, 48, 49, 50, 51, 52, 53, 54, 55, 56, 57, 58, 59, 60, 61, 62, 63, 64, 65, 66, 67, 68, 69, or 70° C. for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 seconds allowing annealing of the primers in a primer set to hybridize with a target nucleic acid. The annealing temperature can be about 0, 1, 2, 3, 4, 5, 6, 7, 8, 9, or 10° C. below the Tm of the primers used. Stable DNA-DNA hydrogen bonds are formed when the primer sequence very closely matches the template sequence. The polymerase binds to the primer-template hybrid and begins DNA synthesis.

The extension/elongation step is the step where the nucleic acid polymerase synthesizes a new nucleic acid strand complementary to the target nucleic acid strand by adding dNTPs that are complementary to the target nucleic acid in 5' to 3' direction, condensing the 5'-phosphate group of the dNTPs with the 3'-hydroxyl group at the end of the nascent (extending) target nucleic acid strand. The extension time depends both on the nucleic acid polymerase used and on the length of the target nucleic acid to be amplified. As a rule-of-thumb, at its optimum temperature, the nucleic acid polymerase will polymerize a thousand bases per minute. Under optimum conditions, i.e., if there are no limitations due to limiting substrates or reagents, at each extension step, the amount of target nucleic acid is doubled, leading to exponential (geometric) amplification of the specific target nucleic acid. The elongation temperature at this step depends on the nucleic acid polymerase used. For example; Taq polymerase has its optimum activity temperature at 75-80° C., and commonly a temperature of 72° C. is used with this enzyme.

PCR can also comprise a final elongation step. The final elongation can be performed at a final elongation temperature of 68, 69, 70, 71, 72, 73, 74 or 75° C. for 1, 2, 3, 4, 5, 6, 7, 8, 9, 10, 11, 12, 13, 14, or 15 minutes after the last PCR cycle to ensure that any remaining single-stranded DNA is fully copied to make a double-stranded DNA product.

PCR can also comprise a signal acquisition step wherein the amount of a detection label can be determined. The signal acquisition step can be carried out during the amplification of the target sequence. In some aspects the signal acquisition step follows a denaturation step, an annealing step and an elongation steps. The signal acquisition step is carried out at a signal acquisition temperature. The signal acquisition temperature can be any temperature and can be carried out at one or more times during PCR. When the copy number of two or more target nucleic acids are being determined as described herein, the signal acquisition temperature should be different for detection of the detection label of each amplicon. For example, the temperatures for the two or more signal acquisition temperature should be selected such that the first signal acquisition temperature is below the Tm of the first amplicon and the second signal acquisition temperature is above said first Tm and below the Tm of the second amplicon. The difference between the two or more signal acquisition temperatures can be 3, 4, 5, 6, 7, 8, 9, or 10° C. A Signal Acquisition Step can be carried out for 1, 2, 3, 4, 5, 6, 7, 8, 9, 10, 11, 12, 13, 14, or 15 seconds at the acquisition temperature.

PCR can also comprise a final hold step. The final hold step can be at a final hold temperature of: This step at 4, 5, 6, 7, 8, 9, 10, 11, 12, 13, 14, or 15° C. for an indefinite time. The final hold step can be employed for short-term storage of the reaction.

The polymerase chain reaction can also comprise consecutive stages of cycles. Each consecutive stage of cycles can comprise one or more of the PCR steps described above. Each consecutive stage of cycles can also be referred to a "cycle" of the PCR. Each consecutive stage of cycles can be carried out under the same or different temperatures for each cycle of the PCR. A PCR can be run where the annealing temperature is changed for one or more of the cycles of PCR. For example, the PCR can be run for a total of 40 cycles, wherein the annealing temperature is the same for a first stage of cycles, then the annealing temperature is raised for a second stage of cycles and the annealing temperature is lowered for the third stage of cycles.

A "homogenous system" is a system wherein amplification and detection of a target nucleic acid takes place in the same reaction. A homogenous system is one which generates a detectable signal during the amplification of a target sequence. By "during the amplification" is meant that after a cycle of PCR, but prior to a subsequent cycle of PCR. "During the amplification" is also meant to mean during PCR, but prior to a final hold step.

The relative copy number can be carried out by the methods described elsewhere herein. For example, the methods described herein can be used to measure the amounts of telomere (T) repeat sequences in experimental DNA samples in one set of reaction wells, and the amount of single copy genes (S) in separate wells, in comparison to a reference DNA, to yield relative T/S ratios that are proportional to average telomere length. In one aspect, the T signals can be collected in early cycles, before S signals rise above baseline, and S signals can be collected at a temperature that fully melts the telomere product, sending its signal to baseline. The correlation of T/S ratios can also be correlated with Terminal Restriction Fragment (TRF) lengths measured by Southern blot to determine copy numbers.

Also disclosed herein are methods for determining the copy number of a first target nucleic acid and a second target nucleic acid, wherein the copy number of the first target nucleic acid sequence is greater than the copy number of the second target nucleic acid sequence, comprising: a) contacting a first target nucleic acid with a first primer set and a second target nucleic acid, with a second primer set and adding a single detection label to form a reaction mixture in a homogenous system, b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) until the detection label is determined at said second signal acquisition temperature; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm, wherein the amount of the detection label is detected at said first and said second signal acquisition temperatures during each of said amplification steps; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm, wherein the difference between the first Tm and the second Tm is at least 4 degrees Celsius; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, wherein at least one of the primers in the second primer set comprises a GC-clamp at the 5' end of the primer b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, wherein at least one of the primers in said first primer set comprises a 5' sequence that includes A and T nucleotides b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, wherein the 3' ends of the primers of the first primer set are complementary to each other and wherein one primer of the first primer set is a mismatch primer comprising at least one mismatched nucleotide adjacent to the 3' end of the primer, wherein said nucleotide is not complementary to the target nucleic acid, but is complementary to the 3' terminal nucleotide of the other primer in the first primer set. b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, wherein one of the primers of the first primer set is blocked from priming the first target nucleic acid b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

Also disclosed herein are methods for determining the copy number of a first target nucleic acid and a second target nucleic acid, comprising: a) contacting a first target nucleic acid with a first primer set and a second target nucleic acid, with a second primer set and adding a single detection label to form a reaction mixture in a homogenous system, wherein the detection label is an intercalating dye b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

In some aspects of the methods described herein, the copy number of the first and the second target nucleic acids measures the relative amount of the first nucleic acid as compared to the second nucleic acid.

In some aspects Target and reference sequences can be accurately quantitated in a multiplex QPCR using SYBR Green I as the only fluorescent dye and QPCR machines equipped only for single color detection, by a strategy that prevent the amplification of the earlier amplifying template from interfering with the amplification of the later amplifying template. In some aspects, to quantitate two templates in a set of DNA samples by MMQPCR, two requirements must be met. First, PCR conditions must be found such that, for each DNA sample in the set, when the cycle threshold for the earlier-amplifying product is reached, the amplification signal from the later-amplifying product is still at baseline. Second, the later-amplifying product must have a higher melting temperature than the earlier-amplifying product, so that the later-amplifying product's fluorescence can be monitored at a temperature low enough to keep it double-stranded, but high enough to completely melt the earlier-amplifying product, sending its fluorescence signal to baseline. By designing primers to keep both PCR products small, and adding GC-rich 5' tags such as GC-clamps to the primers for the later-amplifying product, one can ensure that the later-amplifying product will have the higher melting temperature.

The methods described herein can be used to quantitate the levels of two different templates in a biological sample, where each template varies in copy number, and yet there is no overlap in the ranges of copy number of the first and second templates. For example, cells have far more copies of telomere repeats than copies of single copy nuclear genes; the same situation applies for mtDNA copies vs. single copy genes, rDNA copies vs. single copy genes, Alu DNA copies vs. single copy genes, etc. Similarly, in multiplex reverse transcriptase QPCR (RT-QPCR) studies of mRNA levels, the aim often is to quantify the levels of two different mRNA species, each varying in copy number, but with non-overlapping ranges of copy number. For each of these pairs of templates, the $C_t$ for the more abundant template can be collected when the amplification signal from the less abundant template is at baseline; and the $C_t$ for the less abundant template can be collected at a high temperature that leaves its GC-rich product double-stranded, while completely melting and eliminating the signal from the product of the abundant template. By collecting fluorescence signals at two different temperatures throughout the PCR cycling, and analyzing those signals separately, one can quantitate each of the two templates independently with a single, monochrome detection label.

To date, it has been presumed impossible to determine the relative copy numbers of two different DNA sequences in a multiplex quantitative polymerase chain reaction using a single DNA-intercalating dye, because the accumulating fluorescent signal arises from both amplicons. The methods described herein present a strategy that allows the signals from the two amplicons to be collected separately. The cycle thresholds ($C_t$s) for the first amplicon are collected at earlier cycles, when the signal from the second amplicon is still at baseline. The $C_t$s for the second amplicon are collected at a temperature well above the melting temperature ($T_m$) of the first amplicon, rendering the first amplicon single-stranded and sending its signal to baseline. Primers are designed to make both amplicons small, and the second amplicon GC-rich, raising its $T_m$. Pairs of templates that occur in biological samples as high and low abundance species with no overlap in copy number ranges are natural targets for this approach. Even two templates with similar copy numbers can be distinguished by applying primer and thermal cycling designs that delay the amplification of one amplicon. The methods described herein can be used to determine the relative telomere lengths in human DNA samples.

Similar Copy Number Methods

Also disclosed herein are methods determining the copy number of a first target nucleic acid and a second target nucleic acid, wherein the copy number of the first target nucleic acid sequence is similar to the copy number of the second target nucleic acid sequence comprising: a) contacting a first target nucleic acid with a first primer set and a second target nucleic acid, with a second primer set and adding a single detection label to form a reaction mixture in a homogenous system, b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first Tm and below said second Tm; e) repeating steps (b) through (d) at least one time; and f) determining the relative copy number of said first and said second target nucleic acids.

When the copy number of the first target nucleic acid sequence is similar to the copy number of the second target nucleic acid sequence the cycles of the PCR or the individual steps of the PCR can be altered or changed. For example, when the copy number of the first target nucleic acid sequence is similar to the copy number of the second target nucleic acid sequence the polymerase chain reaction of this method can further comprise at least three consecutive stages, wherein the first stage of the polymerase chain reaction comprises a polymerase chain reaction cycle wherein the annealing temperature of the polymerase chain reaction is higher than the annealing temperature of the second stage, wherein the second stage of the polymerase chain reaction comprises a polymerase chain reaction cycle wherein the annealing temperature of the polymerase chain reaction is lower than the annealing temperature of the first stage, and wherein the third stage of the polymerase chain reaction comprises a polymerase chain reaction wherein the annealing temperature of the polymerase chain reaction is lower than the annealing temperature of the first stage and higher than the annealing temperature of the second stage.

In some aspects, when consecutive stages of the polymerase chain reaction are employed, only the second amplicon is formed during the first stage of the polymerase chain reaction. In some aspects, when consecutive stages of the polymerase chain reaction are employed only the first amplicon is formed during the second stage of the polymerase chain reaction. In some aspects, when consecutive stages of the polymerase chain reaction are employed both the first and second amplicons are formed during the third stage of the polymerase chain reaction. In some aspects, when consecutive stages of the polymerase chain reaction are employed only the second amplicon is formed during the first stage of the polymerase chain reaction and only the first amplicon is formed during the second stage of the polymerase chain reaction and both the first and second amplicons are formed during the third stage of the polymerase chain reaction.

Primer composition and the various temperature of the PCR can also be altered depending on the target and Tm of the primers, amplicons and polymerases being used or generated.

In some aspects, to quantitate two templates of similar abundance by MMQPCR, the amplification of one of the templates is delayed by several cycles. For example, one primer pair can be designed to anneal at 68° C., and the other pair at 50° C. After the initial 15 minute activation of the hot-start DNA polymerase and denaturation of the genomic DNA sample, cycling between 94° C. and 68° C. for at least four cycles would provide a 4 cycle (or more) head start in amplification for the first template, leaving the second template unprimed. Next, cycling between 94° C. and 50° C. for two cycles would continue amplifying the first template, but also initiate amplification from the second template. Note that the primers for the second template can have the GC-rich 5' tags, such as GC-clamps, to confer a high melting temperature on their PCR product. Since cycling between 94° C. and 50° C. for two cycles is sufficient to synthesize sequences complementary to the full length of these primers, it follows that once those two cycles are completed, the annealing temperature can be raised again, and the remaining cycles in the program can have a thermal profile similar to that of Stage 3 in the protocol below (see Materials and Methods), during which the fluorescence signal is collected at two different temperatures in each cycle.

In another aspect, a second approach to delaying the amplification of one template by several cycles is provided to allow both primer pairs to initiate product formation; then to apply four or more cycles with a denaturation temperature high enough to melt the low-melting amplicon but not high enough to melt the high-melting amplicon; and finally to switch to a thermal profile similar to that of Stage 3 (see Materials and Methods) for the remaining cycles. The stage of cycling with a lowered denaturation temperature may still allow a linear amplification from the original template, which amplification was intended to be delayed. A solution to this problem is to use both primer pairs having a relatively low initial annealing temperature, e.g. 50° C., but higher subsequent annealing temperatures for the PCR amplicons, conferred by 5' tags, such as GC-clamps. By cycling between 94° C. and 50° C. for two cycles, a sufficient to generate the initial PCR products, after which the annealing temperature would be raised enough to prevent any further priming of the original DNA templates.

In one aspect the first target nucleic acid is in a first nucleic acid and said second target nucleic acid is in a second nucleic acid. In this aspect the copy number of the first and the second target nucleic acids measures the relative amount of said first nucleic acid as compared to said second nucleic acid. In another aspect, the first target nucleic acid is in a first nucleic acid and the second target nucleic acid is in a second nucleic acid. The copy number of the first target nucleic acid measures non tandem repeats of the first target nucleic acid in the first nucleic acid where the non tandem repeats are independently amplified by said first primer pair.

Also disclosed are methods for determining the copy number of a first target nucleic acid as compared to the copy number of a second target nucleic acid by multiplex quantitative PCR. The first target nucleic acid comprises tandem repeats and the copy number of said first target nucleic acid sequence is greater than the copy number of said second target nucleic acid sequence. The method comprises: (1) contacting a sample comprising the first target nucleic acid and the second target nucleic acid with a first primer set, a second primer set and an intercalating dye, wherein the first primer set is capable of PCR amplifying the first target nucleic acid to form a first amplicon having a first melting temperature (Tm), wherein a first primer of the first primer pair comprises a mismatched nucleotide at other than the 3' terminus that does not base pair with a nucleotide in a first strand of said first target nucleic acid when said first primer is hybridized to said first strand and wherein the second primer of said first primer pair has a 3' nucleotide that does not base pair with a nucleotide in the second strand of said first nucleic acid but does base pair with said mismatched nucleotide in a PCR transcript of said first strand when said second primer is hybridized to said PCR transcript, whereby the first amplicon produced by repeated PCR cycles has a defined size with said first Tm and wherein said second primer set is capable of amplifying said second target nucleic acid to form a second amplicon having a second Tm, where said second Tm is greater than said first Tm; (2) PCR cycling the sample through a temperature profile that includes first and second signal acquisition temperatures for measuring intercalation of the dye in the first and second amplicons, where the first signal acquisition temperature is below the first Tm and said second signal acquisition temperature is above the first Tm and below the second Tm; (3) repeating the PCR cycling step; and (4) measuring the intercalation signal from the intercalation of the dye at the first and said second signal acquisition temperatures during at least two different PCR cycles to determine the relative copy number of the first and the second target nucleic acids.

Also disclosed are methods for determining the copy number of a first target nucleic acid as compared to the copy number of a second target nucleic acid by multiplex quantitative PCR, where the copy number of the first target nucleic acid sequence is similar to the copy number of the second target nucleic acid sequence. The method comprises: (1) contacting a sample comprising the first target nucleic acid and the second target nucleic acid with a first primer set, a second primer set and an intercalating dye, wherein the first primer set is capable of amplifying the first target nucleic acid to form a first amplicon having a first melting temperature (Tm) and wherein the hybridization complex between the first primer pair and the first target nucleic acid has a first primer Tm and wherein the second primer set is capable of amplifying the second target nucleic acid to form a second amplicon having a second Tm and wherein the hybridization complex between said second primer pair and said second target nucleic acid has a second primer Tm, where said second Tm is greater than said first Tm and wherein said first primer Tm is greater than said second primer Tm; (2) subjecting said sample to a predetermined number of PCR cycles wherein the primer annealing temperature during said predetermined PCR cycles is above said second primer Tm to prevent amplification of said second target nucleic acid; (3) PCR cycling said sample through a temperature profile wherein the primer annealing temperature is at or below said second primer Tm whereby said first and said second target nucleic acids are PCR amplified and wherein said temperature profile includes first and second signal acquisition temperatures for measuring intercalation of said dye in said first and second amplicons, where said first signal acquisition temperature is below said first Tm and said second signal acquisition temperature is above said first Tm and below said second Tm; (4) repeating said PCR cycling step; and (5) measuring the intercalation signal from the intercalation of said dye at said first and said second signal acquisition temperatures during at least two different PCR cycles, wherein the relative copy number of said first and said second target nucleic acids is determined from said intercalation signals and said predetermined number of PCR cycles.

Also disclosed are methods for determining the copy number of a first target nucleic acid as compared to the copy number of a second target nucleic acid by multiplex quantitative PCR, wherein the copy number of said first target nucleic acid sequence is similar to the copy number of said second target nucleic acid sequence. The method comprises: (1) contacting a sample comprising said first target nucleic acid and said second target nucleic acid with a first primer set, a second primer set and an intercalating dye, wherein said first primer set is capable of amplifying said first target nucleic acid sequence to form a first amplicon having a first melting temperature (Tm) and wherein the hybridization complex between said first primer pair and said first target nucleic acid has a first primer Tm and said second primer set is capable of amplifying said second target nucleic acid to form a second amplicon having a second Tm and wherein the hybridization complex between said second primer pair and said second target nucleic acid has a second primer Tm, where said second Tm is greater than said first Tm and wherein said first primer Tm is greater than said second primer Tm; (2) subjecting said sample to a first predetermined number of PCR cycles wherein the primer annealing temperature during said predetermined PCR cycles is at or below said first primer Tm to amplify said first and said second target nucleic acids; (3) subjecting said sample to a second predetermined number of PCR cycles wherein the denaturation temperature is below said second Tm to prevent further amplification of said second target nucleic acid; (4) PCR cycling said sample through a temperature profile wherein the primer annealing temperature is at or below said second primer Tm whereby said first and said second target nucleic acids are PCR amplified and wherein said temperature profile includes first and second signal acquisition temperatures for measuring intercalation of said dye in said first and second amplicons, where said first signal acquisition temperature is below said first Tm and said second signal acquisition temperature is above said first Tm and below said second Tm; (5) repeating said PCR cycling step; and (6) measuring the intercalation signal from the intercalation of said dye at said first and said second signal acquisition temperatures during at least two different PCR cycles, wherein the relative copy number of said first and said second target nucleic acids is determined from said intercalation signals and said second predetermined number of PCR cycles.

In some aspects of the methods described herein a second sample can be used as a reference for measuring copy number. The methods further comprise at least one reference sample comprising a reference nucleic acid comprising known copy numbers of said first and said second target nucleic acids, said first and said second primer pairs and said intercalating dye; wherein said second sample is subjected to the same PCR conditions as said first sample and wherein the intercalation signals at said first and said second signal acquisition temperatures for said second sample are compared to the intercalation signals at said first and second signal acquisition temperatures in said first sample to provide an indication of the absolute copy number of said first and said second target nucleic acids.

In some aspects the methods comprise: (1) contacting a sample comprising said first target nucleic acid with a first primer set and said second target nucleic acid with a second primer set, wherein said first primer set is capable of amplifying said first target nucleic acid to form a first amplicon having a first melting temperature (Tm) and said second primer set is capable of amplifying said second target nucleic acid to form a second amplicon having a second Tm, where said second Tm is sufficiently greater than said first Tm to ensure that said first amplicon is completely melted at a temperature at which said second amplicon has not yet begun to melt; in the presence of any single detection label that fluoresces upon intercalation into double-stranded DNA; (2) repeated PCR cycling said sample through a temperature profile that includes first and second signal acquisition temperatures for measuring intercalation of said dye in said first and second amplicons, where said first signal acquisition temperature is sufficiently below said first Tm that said first amplicon has not yet begun to melt and said second signal acquisition temperature is sufficiently above said first Tm that the first amplicon is completely melted and sufficiently below said second Tm that the second amplicon has not yet begun to melt; and (3) measuring the intercalation signal from said dye at said first and said second signal acquisition temperatures during at least two different PCR cycles to determine the relative copy number of said first and said second target nucleic acids, under a set of conditions that allows said first signal to cross the threshold of detection at a cycle number at which said second signal is still at baseline.

Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for determining the copy number of one or more target nucleic acids, the kit comprising one or more reagent compositions and one or more components or reagents for determining the copy number of one or more target nucleic acids. For example, the kits can include one or more reagent compositions and one or more primer sets, a detection label, a nucleic acid polymerase, or a combination. Another form of kit can comprise a plurality of reagent compositions. The kits also can contain, for example, nucleotides, buffers, ligase, open circle probes, gap oligonucleotides, or a combination.

Disclosed are kits that can be used in such methods. The kits can include at least first and second PCR primer pairs for amplifying the first and second target nucleic acids. Such components can be in a first container that is adapted to be used in a PCR amplification machine. In one aspects, the test sample is added to the container and PCR amplification is carried out according to the disclosed methods. The kits can also include one or more, or all, of the components for carrying out PCR including deoxynucleotide triphosphates, thermostable DNA polymerase and a detection label.

In one aspect, the kit can comprise a second container, also adapted for use in a PCR machine, containing a second sample comprising a reference nucleic acid comprising known copy numbers of the first and said second target nucleic acids and optionally the other components needed for carrying out PCR, including the first and second primer pairs and an intercalating dye. This second container is subjected to the same PCR conditions as the first container sample. The second container provides reference intercalation signals for known copy numbers of the first and second target nucleic acids thereby facilitating the determination of the absolute copy number of first and said second target nucleic acids in a test sample. Additional containers containing reference nucleic acids having different copy numbers of the first and second target nucleic acids can also be included in the kit. Such containers provide additional intercalation signals that provide different reference points over a range of absolute copy number ratios. Such additional containers are particularly useful when the copy number of the first and second target nucleic acids in a test sample can vary over a wide range.

Also disclosed are kits having a first container, adapted for use in a PCR machine, where said first container comprises a reference nucleic acid comprising known copy numbers of the first and second target nucleic acids. The kit may further comprise at least one additional container comprising a second reference nucleic acid having a different copy number of the first and second target nucleic acids as compared to the reference nucleic acid of said first container. The containers optionally contain an intercalating dye and the other components needed for PCR. Such kits are useful in standardizing the intercalation signals from a PCR machine for one or more different reference nucleic acids.

Systems

Disclosed are systems useful for performing, or aiding in the performance of, the disclosed method. Also disclosed are systems for producing reagent compositions. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising solid supports and reagent compositions.

Data Structures and Computer Control

Disclosed are data structures used in, generated by, or generated from, the disclosed method. Data structures generally are any form of data, information, and/or objects collected, organized, stored, and/or embodied in a composition or medium. A target fingerprint stored in electronic form, such as in RAM or on a storage disk, is a type of data structure.

The disclosed method, or any part thereof or preparation therefore, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

EXAMPLES

Example 1

Research Subjects

Genomic DNA was extracted directly from blood samples by standard procedures, and stored long-term in $TE^{-4}$ (10 mM Tris-HCl, 0.1 mM EDTA, pH 7.5) at 4° C. at a concentration of approximately 100 ng per microliter. DNA stocks were diluted into pure water just prior to setting up QPCR runs. The samples, from 95 Utah individuals (47 females and 48 males, age range 5-94 years), are those analyzed in our previous paper describing telomere length measurement by monoplex quantitative PCR (Cawthon, R. M. (2002) Telomere measurement by singleplex quantitative PCR. *Nucleic Acids Res*, 30, e47).

Monochrome Multiplex Quantitative PCR (MMQPCR)

PCR reactions were set up by aliquoting 15 microliters of master mix into each reaction well of a 96-well plate compatible with the Bio-Rad MyiQ Single Color Real-Time PCR Detection System, followed by 10 microliters of each experimental DNA sample, containing approximately 20 nanograms of DNA diluted in pure water, for a final volume of 25 microliters per reaction. Five concentrations of a reference DNA sample (the "Standard DNA") spanning an 81-fold range of DNA concentration were prepared by serial dilution and analyzed in duplicate in every 96-well plate in this study; these reactions provided the data for the generation of the standard curves used for relative quantitation. All experimental DNA samples were assayed in triplicate.

The final concentrations of reagents in the PCR were 0.75×SYBR Green I (Invitrogen), 10 mM Tris-HCl pH 8.3, 50 mM KCl, 3 mM $MgCl_2$, 0.2 mM each dNTP, 1 mM DTT, and 1M betaine (U.S. Biochemicals). Each 25 microliter reaction received 0.625 U AmpliTaq Gold DNA polymerase (Applied Biosystems, Inc.).). For multiplex QPCR, the telomere primer pair telg and telc (final concentrations 900 nM each), were combined either with the albumin primer pair albu and albd (final concentrations 900 nM each), or with the beta-globin primer pair hbgu and hbgd, (final concentrations 500 nM each) in the master mix. All primer sequences and the rationale for their design are presented in the Results section.

The thermal cycling profile was Stage 1: 15 min at 95° C.; Stage 2: 2 cycles of 15 s at 94° C., 15 s at 49° C.; and Stage 3: 32 cycles of 15 s at 94° C., 10 s at 62° C., 15 s at 74° C. with signal acquisition, 10 s at 84° C., 15 s at 88° C. with signal acquisition. The 74° C. reads provided the $C_t$s for the amplification of the telomere template; the 88° C. reads provided the $C_t$s for the amplification of the single copy gene template.

After thermal cycling and raw data collection were complete, the MyiQ software (Bio-Rad iQ5 2.0 Standard Edition Optical System Software) was used to generate two standard curves for each plate, one for the telomere signal and one for the scg signal. The T/S ratio for an experimental DNA sample is T, the number of nanograms of the Standard DNA that matches the experimental sample for copy number of the telomere template, divided by S, the number of nanograms of the Standard DNA that matches the experimental sample for copy number of the scg. As each experimental sample was assayed in triplicate, three T/S results were obtained for each sample; the final reported result for a sample in a given run is the average of the three T/S values. Average T/S is expected to be proportional to the average telomere length per cell. Samples with a T/S>1.0 have an average telomere length greater than that of the Standard DNA; samples with a T/S<1.0 have an average telomere length shorter than that of the Standard DNA.

Determination of Mean Terminal Restriction Fragment (TRF) Lengths

Mean TRF lengths were determined in duplicate as described previously (Cawthon, R. M. (2002) *Nucleic Acids Res*, 30, e47). Briefly, DNA was digested with HaeIII restriction endonuclease, and digested samples were mixed with DNA size standards prior to agarose gel electrophoresis and Southern blotting onto nylon membranes. Following hybridization of the blots with a radioactive telomeric oligonucleotide probe ((TTAGGG)$_7$ SEQ ID NO:1) and capture of the telomere smear images, blots were stripped and hybridized with radioactive probes specific for the DNA size standards. The size standard images and telomere smear images were then superimposed to locate the positions of the size intervals within the telomere smears. Mean TRF length was then calculated as $\Sigma(OD_i)/\Sigma(OD_i/L_i)$, where $OD_i$ is total radioactivity above background in interval i and $L_i$ is the average length of i in basepairs.

Results

Primers that Amplify a Fixed-Length Product from Telomeric Tandem Hexamer Repeats Relative average telomere length can be measured by quantitative PCR using primers that hybridize the telomeric hexamer repeats, because the number of binding sites for the primers increases as average telomere length increases. Our original tel1 and tel2 primers for telomere length measurement by singleplex QPCR (1) are both able to prime at multiple locations along the tandem repeats of telomeric DNA. They therefore generate a series of products of various sizes, some of which melt at temperatures high enough to overlap the melting curve of the scg's amplicon. Consequently, "clean" reads, at a high temperature, of the SYBR Green I fluorescence signal from the scg's double-stranded amplicon, without any interfering signal from double-stranded telomere PCR products, as required for successful MMQPCR, are not possible when tel1 and tel2 are the telomere primers.

Figure 2:
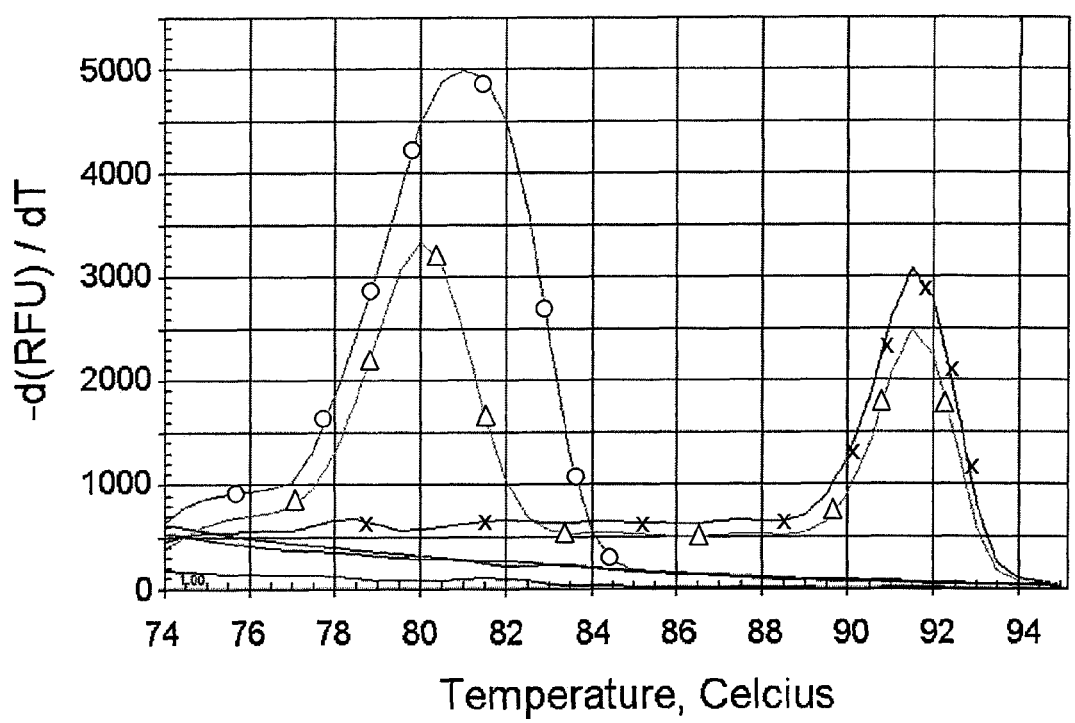
FIG. 2 shows the melting curves following 25 cycles of amplification (thermal profile given in Materials and Methods section) of 150 ng of human genomic DNA with telomere primers only (circles), albumin primers only ("x"s), or both primer sets (triangles). No template control melting curves are in black with no symbols. After the final 88° C. incubation, reactions were cooled to 72° C., and signal was acquired from 72° C. to 95° C., in 0.5° C. steps, with a 30 second dwell period per step. There is approximately an 11° C. difference in the melting temperatures of the telomere and albumin amplicons.

To solve this problem, a pair of telomere primers were designed, telg, ACACTAAGGTTTGGGTTTGGGTTT-GGGTTTGGGTTAGTGT SEQ ID NO:2) and telc, TGT-TAGGTATCCCTATCCCTATCCCTATCCCTATC-CCTAACA SEQ ID NO:3), that generate a short, fixed-length product (FIG. 1). Only telg is able to prime DNA synthesis along native telomeric DNA sequences. The telc primer is blocked from priming native telomeric DNA by a mismatched base at its 3' terminus. However, telc is able to hybridize along various stretches of the telg primer extension product, and exactly one configuration of those hybridizations allows the priming of DNA synthesis, thereby enabling the generation of a single, fixed-length product. This is achieved by introducing a nucleotide change in telg at the third base from the 3' end, such that the last 3 bases of the telg and telc primers overlap with perfect complementarity. This overlap is not sufficient to allow the native telg and telc primers to prime each other efficiently, so primer dimer formation is undetectable over the range of cycles that telomere length quantitation occurs. However, when the telg extension product is hybridized to telc, this three base overlap is the only site where the 3' end of telc can efficiently prime DNA synthesis. See e.g US Patent Publication 2003/0162266. The resulting PCR product is, therefore, of fixed length, and three bases shorter than the sum of the lengths of the two primers used to generate it. The sharp melting curve for this product (green curve in FIG. 2) is consistent with specific, fixed-length product formation, and agarose gel electrophoresis in 6% gels revealed only the expected 79 bp product (data not shown). FIG. 2 also demonstrates that the melting curve for the telomere PCR product is well separated from the melting curve for the albumin PCR product (blue curve in FIG. 2), allowing the SYBR Green I signal from albumin to be read at a temperature that fully melts the telomere PCR product.

Primer Design for Single Copy Genes (Albumin and Beta-Globin)

Primers were designed so that the scg amplicon would melt at a much higher temperature than the telomere amplicon. Fluorescent signal from the scg amplicon could then be acquired at a temperature high enough to completely melt the telomere amplicon, eliminating its contribution to the signal, but low enough to keep the scg amplicon double-stranded and therefore able to bind SYBR Green I.

The primers for amplification of the scg albumin are albu: CGGCGGCGGGCGGCGCGGGCTGGGCGGaaatgctg-cacagaatccttg SEQ ID NO:4); and albd: GCCCGGCCCGC-CGCGCCCGTCCCGCCGgaaaagcatggtcgcctgtt SEQ ID NO:5). The predicted product size is 98 bp. The primers for amplification of the scg beta-globin are hbgu: CGGCG-GCGGGCGGCGCGGGCTGGGCGGcttcatccacgttcaccttg SEQ ID NO:6); and hbgd: GCCCGGCCCGCCGCGC-CCGTCCCGCCGgaggagaagtctgccgtt SEQ ID NO:7). The predicted product size is 106 bp. Capitalized bases are non-templated 5'tag sequences that confer a very high melting temperature on the resulting PCR product. Please note that the 5' tag sequences for the albumin primers are identical to those used in the beta-globin primers. Note also that the two GC-rich 5' tagging sequences in each primer set are very different from each other; if they were the same, hairpin formation shutting down amplification would be likely to occur during the PCR.

The addition of a GC-clamp to the 5' end of a PCR primer to raise the melting temperature of one end of the PCR product is common practice when screening a gene for point mutations by Denaturing Gradient Gel Electrophoresis (2). By attaching 5' GC-clamps to both of the primers used to amplify the scg, and keeping the targeted genomic sequence short, a PCR product with a very high melting temperature will be generated. FIG. 2 shows that the $T_m$ for the doubly GC-clamped albumin PCR product is above 9° C. Agarose gel electrophoresis in 6% gels revealed only the expected size product. Similar results were obtained for the doubly GC-clamped beta-globin PCR product (data not shown).

The 5' GC-clamps also ensure that both of the primers used to amplify the scg have $T_m$s for their amplicon that are higher than the $T_m$ of the telomere PCR product. The benefits of this design are discussed below (see Thermal profile and cycling design). An analysis using the OligoAnalyzer program (www.idtdna.com) indicated that all four scg primers (albu, albd, hbgu, and hbgd) have $T_m$s greater than 84° C. in the buffer composition used in this study.

Thermal Profile and Cycling Design

In Stage 1 of the thermal cycling protocol, the AmpliTaq Gold DNA polymerase is heat-activated, and the genomic DNA sample is denatured. In Stage 2, two cycles of relatively low temperature are needed to effectively anneal and extend the telomere primers, due to the presence in those primers of purposely introduced mutations that prevent formation and amplification of primer dimer PCR products (1).

In Stage 3 the repeating cycle begins with a denaturation, an annealing, and an extension step with signal acquisition that are typical of conventional QPCR. These are followed by two unconventional steps: incubation at 84° C. for 10 s, and incubation at 88° C. for 15 s with a second signal acquisition. Heating to 84° C. melts the early-amplifying telomere product, releasing DNA polymerase (which binds double-stranded, but not single-stranded DNA, ref 3) for work on the scg PCR product, where DNA synthesis can proceed, due to the high annealing temperatures (above 84° C.) of the scg primers, and the ability of Taq DNA polymerase to maintain robust activity even at 84° C. (4).

In conventional multiplex PCR, high concentrations of the earliest amplifying product often inhibit subsequent amplification of less abundant templates, due to the above-mentioned binding up of DNA polymerase by the early product. The usual recommended solution is to limit the primer concentrations for the more abundant target sequence, so that less product is formed, leaving enough DNA polymerase unbound and free to continue copying the less abundant template. But lowering primer concentrations often results in a reduced PCR efficiency, or even a complete failure to amplify the target sequence. Reduced efficiencies also contribute to greater variation in $C_t$ values between replicates. The 84° C. incubation step in MMQPCR eliminates the need to limit the primer concentrations for the more abundant template, releasing polymerase from even high concentrations of the corresponding PCR product, so that the second product can be synthesized efficiently.

Heating further to 88° C. for the second signal acquisition step ensures that the telomere PCR product is completely melted and unable to interfere with the collection of the rising SYBR Green I fluorescence signal from the accumulating scg amplicon.

Validity of the MMQPCR Method Over the Natural Range of Telomere Lengths

Figure 3:
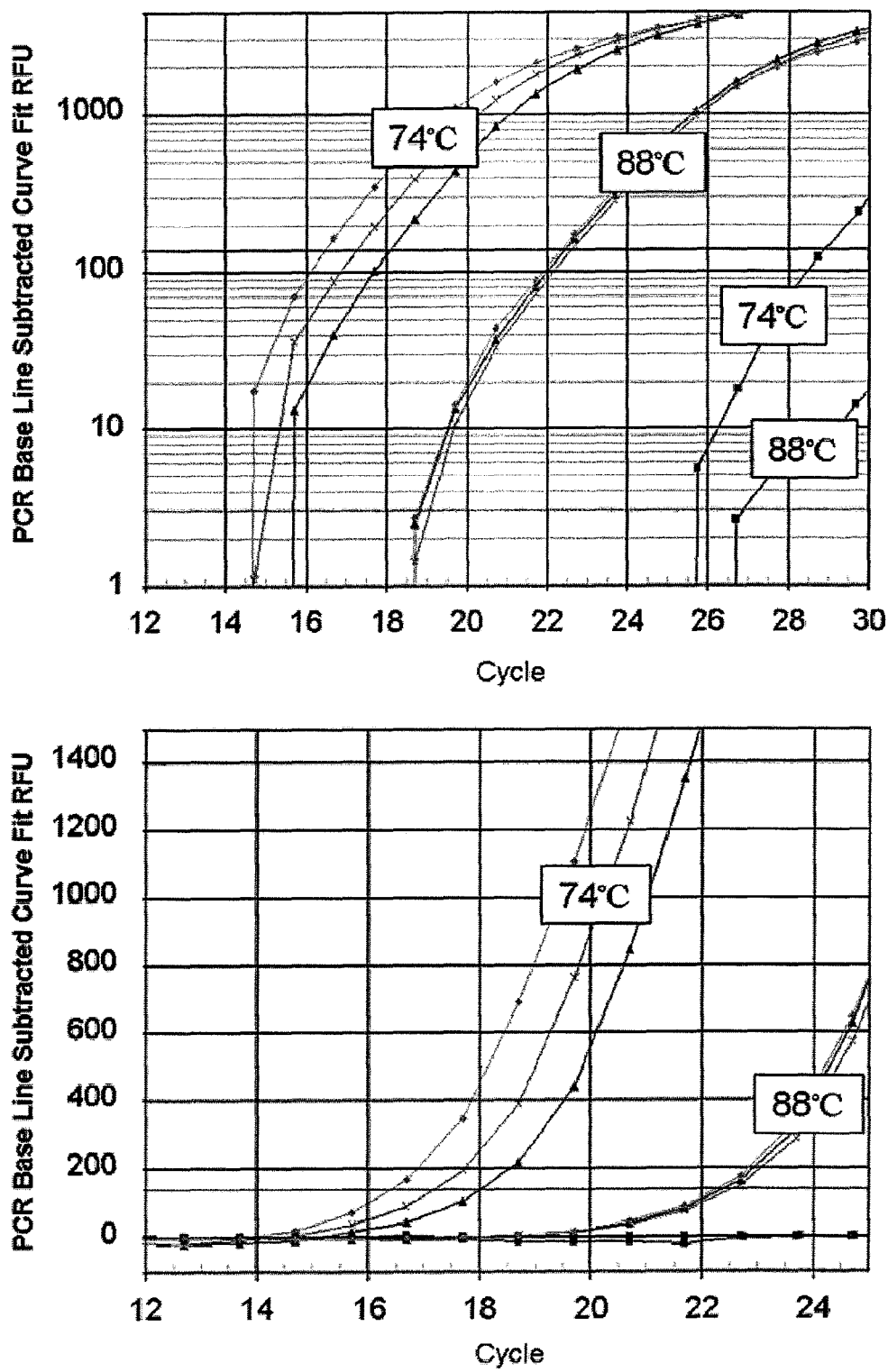
FIG. 3 shows Monochrome Multiplex Quantitative PCR (MMQPCR) of 20 ng of each of three reference human DNA samples previously shown to have long telomeres (circles), middle-length telomeres ("x"s), or short telomeres (triangles). No template control amplification curves are shown with black squares. Top panel: semi-log plot; bottom panel: linear plot.

FIG. 3 shows amplification curves collected at two different temperatures (74° C. and 88° C.) for three reference human genomic DNA samples previously shown to have high, middle, or low average telomere lengths (approximately a 3-fold range of telomere lengths). Based on the melting profiles presented in FIG. 2, the 74° C. reads should detect both telomere and albumin PCR products, and the 88° C. reads should detect only the albumin product. However, because the albumin template is much lower in copy number than the telomere template in each DNA sample, the 74° C. $C_t$s, all collected when the corresponding albumin signals were still at baseline, are measures of telomere amplification only. (It has been confirmed, in reactions without the telomere primers, that the single copy gene signal rises above baseline at essentially the same cycle number whether collected at 74° C. or 88° C.) Even the sample with the shortest telomeres (approximately 1,670 bp), and therefore the most right-shifted amplification curve (blue curve), crosses threshold at a cycle number when the albumin gene's amplification signal is still at baseline. In the present study of 95 whole blood DNA samples from subjects aged 5-94 years, each sample's scg amplification signal was at baseline when the $C_t$ for the corresponding telomere signal was collected.

Independent Standard Curves for Telomere and Single Copy Gene

Figure 4:
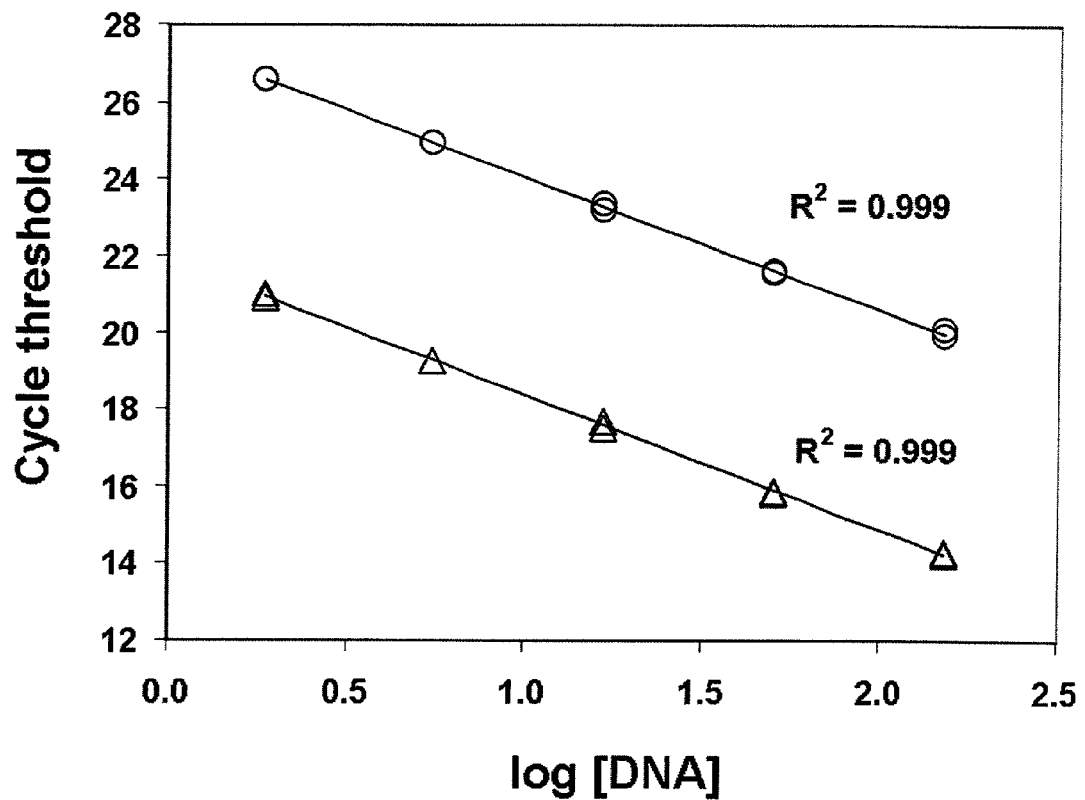
FIG. 4 shows standard curves used to determine relative T/S ratios. Five concentrations of a standard human genomic DNA sample spanning an 81-fold range were prepared by 3-fold serial dilutions (150 ng, 50 ng, 16.7 ng, 5.55 ng, and 1.85 ng per well), and aliquoted in duplicate to a 96-well PCR plate. Both target and reference fluorescent signals were collected from each reaction well. Circles represent data for the single copy gene albumin, acquired at 88° C.; triangles, data for telomere repeats, acquired at 74° C. The same Standard DNA was used to set up standard curve reactions in every plate in the study.

FIG. 4 shows two independent standard curves, one for the telomere repeats and another for the scg albumin, determined for the Standard DNA by acquiring the SYBR Green I fluorescence signal at two different temperatures (74° C. for the telomere signal, and 88° C. for the albumin signal) in each cycle of Stage 3 of the cycling protocol. This same DNA sample was used to generate two standard curves for each separate PCR reaction plate in this study. In this semi-log plot of DNA concentration vs. cycle threshold, both curves are linear over the 81-fold DNA concentration range. The PCR efficiencies for both telomere and albumin amplifications were greater than 90%, and approximately equal. For this particular Standard DNA sample, at each DNA concentration the $C_t$ for albumin occurred approximately six cycles later in cycling than the $C_t$ for the telomere repeats.

In FIG. 3, essentially identical amounts of DNA were inputted into the reactions (based on $OD_{260}$ UV spectrophotometer readings), so that the differences in $C_t$ observed at 74° C. would reflect only differences in telomere length (without influence from variation in the amounts of input DNA). (In normal practice, there is no need to precisely match experimental samples for input DNA, since the procedure of normalizing the T signal to the S signal addresses this issue. A wide range of input DNA amounts are acceptable, as long as both T and S signals fall within the range of the T and S standard curves; see FIG. 4.) The nearly perfect overlap of the three amplification curves acquired at 88° C. is expected, since only the single copy gene (albumin gene) signal is collected at this temperature. The bottom panel shows that the cycle thresholds for the telomere signals can be collected at 74° C. when the albumin signal is still at baseline. (It has been confirmed, in reactions without the telomere primers, that the single copy gene signal rises above baseline at essentially the same cycle number whether collected at 74° C. or 88° C. Also, it has been confirmed, in reactions without the single copy gene primers, that the telomere amplification signal is completely flat and at zero throughout the PCR run when read at 88° C., as would be expected based on the melting profiles shown in FIG. 2.) Since the Bio-Rad MyiQ software can display only one temperature's amplification curves at a time, the displays for the 74° C. and 88° C. reads have been superimposed.

Correlation Between Mean TRF Lengths and Relative T/S Ratios

Figure 5:
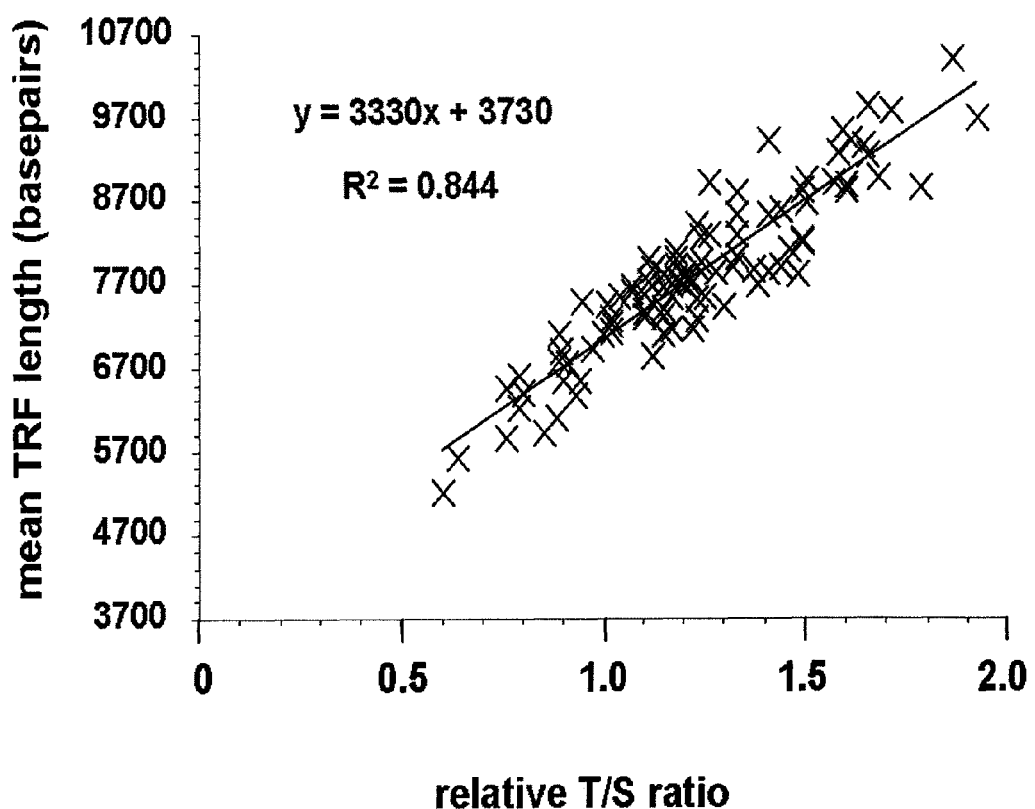
FIG. 5 shows correlation of relative T/S ratios measured by Monochrome Multiplex Quantitative PCR with albumin as the single copy gene, and mean Terminal Restriction Fragment (TRF) lengths determined by Southern blot analysis, in whole blood DNA samples from 95 individuals. Each T/S value is the average of triplicate measurements; each mean TRF length is the average of duplicate measurements. The linear regression equation and correlation coefficient were determined using Microsoft Excel.

To test the validity of the MMQPCR approach to telomere length measurement, the relative telomere lengths (average T/S ratios) in whole blood DNA samples from 95 individuals, aged 5-94 years, measured in triplicate by MMQPCR, were compared to the mean Terminal Restriction Fragment (TRF) lengths of these same DNA samples as measured by the traditional Southern blot approach (1). FIG. 5 shows the strong correlation in relative telomere lengths measured by these very different techniques ($R^2=0.844$). This correlation is higher than the correlation as reported previously (1) for T/S ratios measured in these same samples by singleplex QPCR vs. their mean TRF lengths ($R^2=0.677$).

Reproducibility of T/S Ratio Measurements

Figure 6:
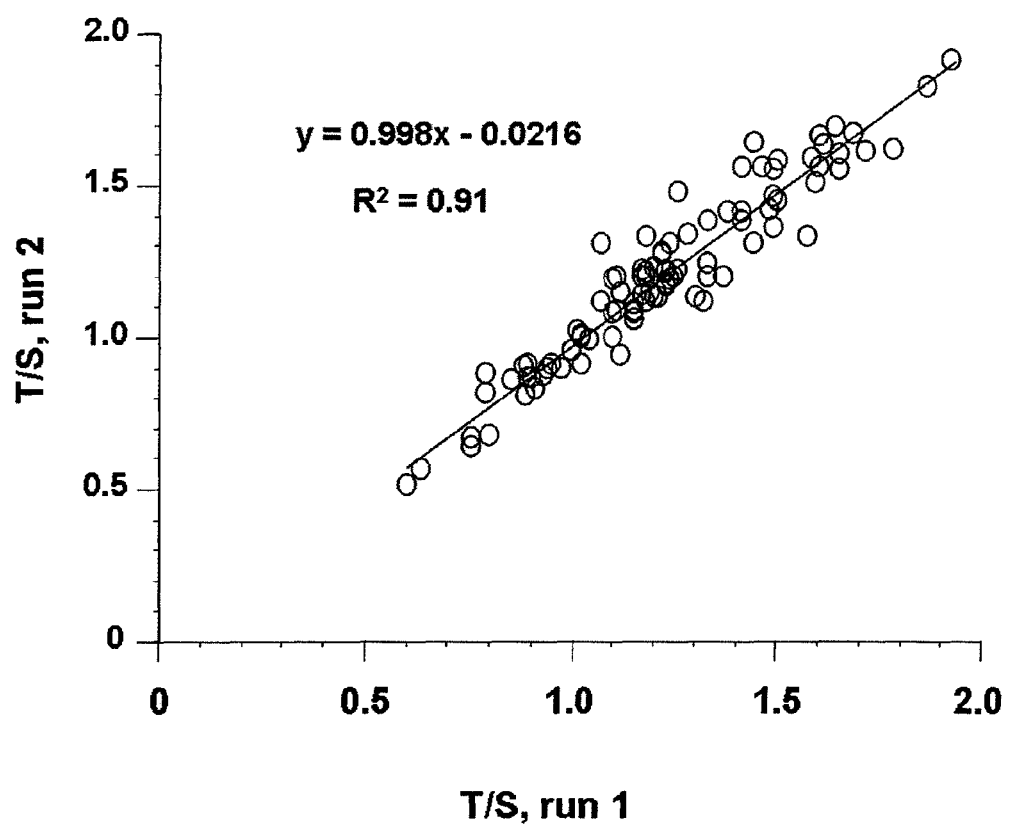
FIG. 6 shows reproducibility of relative T/S ratios in independent runs of the MMQPCR assay. The same 95 DNA samples assayed in FIG. 4 were assayed again the next day, taking care that the specific MyiQ PCR machine and reaction well positions occupied by each DNA sample were different from the previous day. The linear regression equation and correlation coefficient were determined using Microsoft Excel.

To examine the intra-assay reproducibility of T/S measurements by MMQPCR, the coefficient of variation (standard deviation divided by the mean) for T/S was determined for each of the 95 DNA samples assayed in triplicate in a single run of the MMQPCR assay, using albumin as the scg. The intra-assay geometric mean of the coefficient of variation was 5.22%. To examine inter-assay reproducibility, the measurements of T/S in the same 95 DNA samples was repeated, again in triplicate, on another day, taking care that the specific MyiQ PCR machine and reaction well positions occupied by each DNA sample were different in these two independent runs of the assay. FIG. 6 shows the strong correlation between the average T/S ratios determined by the first and second runs ($R^2=0.91$). The slope of the linear regression line through the data was near unity, and the y-intercept near zero, as expected. The coefficient of variation for each of the 95 pairs of average T/S values from the two independent runs was determined. The inter-assay geometric mean of the coefficient of variation was 3.13%.

T/S Ratios are Independent of the Single Copy Gene Used

Figure 7:
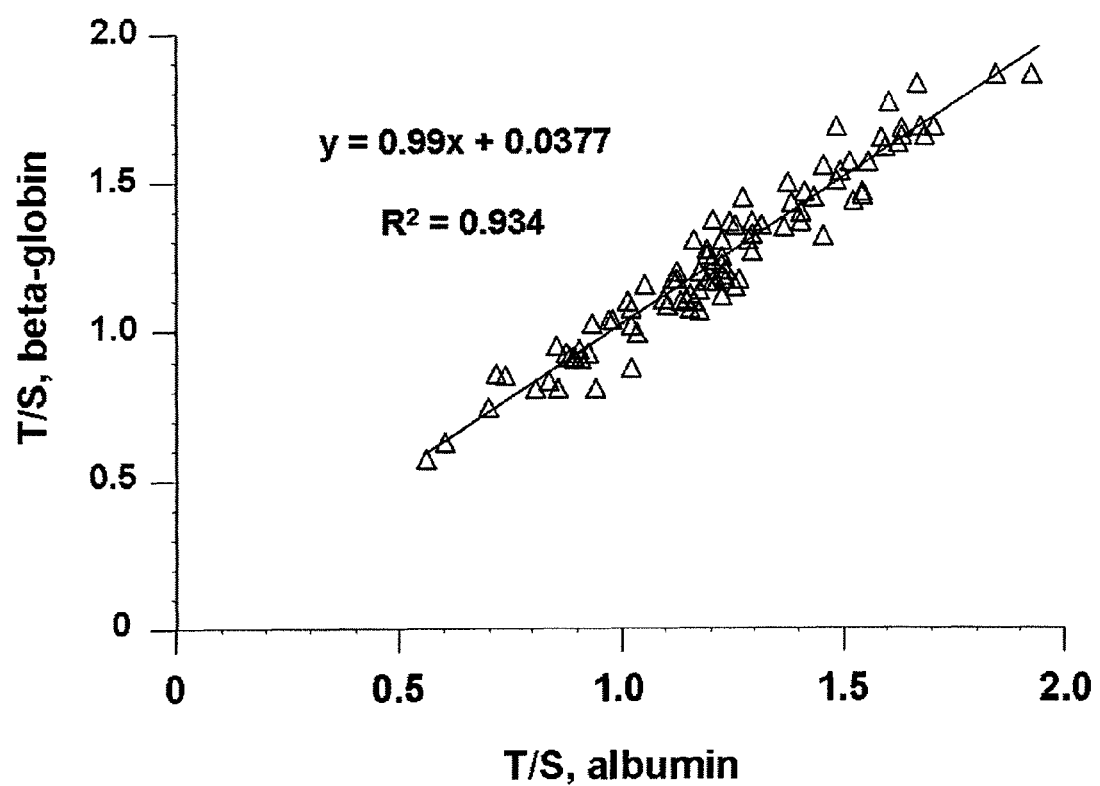
FIG. 7 shows the correlation between T/S ratios obtained with albumin as the single copy gene vs. beta-globin as the single copy gene. Relative T/S ratios were measured in the same 95 DNA samples, in triplicate, in two separate runs, substituting the beta-globin primers for the albumin primers. For each sample, the average T/S from the two separate runs with albumin as the single copy gene (x axis) is plotted against the average T/S from the two runs with beta-globin as the single copy gene (y axis). The linear regression equation and correlation coefficient were determined using Microsoft Excel.

To test whether using beta-globin, instead of albumin, as the scg might alter apparent relative telomere lengths, the measurements of T/S in the same 95 DNA samples were repeated in triplicate, in two separate runs, substituting the beta-globin primers for the albumin primers. FIG. 7 plots the average T/S values from the two runs with albumin as the scg (x axis) vs. the average T/S values from the two runs with beta-globin as the scg (y axis). The T/S values obtained with albumin agree correlated highly with those obtained using beta-globin ($R^2=0.934$).

Relative telomere lengths (T/S ratios) measured in 95 DNA samples by the monochrome multiplex quantitative PCR method described were very highly correlated with relative Terminal Restriction Fragment lengths measured by Southern blot. The T/S ratios measured in these same samples by an original singleplex QPCR assay were not as highly correlated with the TRF lengths. These results suggest that telomere length measurement by MMQPCR is more accurate than telomere length measurement by singleplex QPCR. Furthermore, T/S results obtained by MMQPCR were highly reproducible in independent runs of the assay. Multiplexing the telomere QPCR assay allows increased throughput and lower costs for epidemiologic studies of telomere length. Furthermore, the usual additional cost associated with converting to a multiplex assay, of having to synthesize or purchase expensive custom-made multi-color fluorescent probes is also avoided by adopting this method.

MMQPCR can be easily adapted for the study of many pairs of DNA templates that naturally occur at very different copy numbers, e.g. mtDNA copies vs. single copy genes, rDNA copies vs. single copy genes, and Alu DNA copies vs. single copy genes. Similarly, pairs of RNA species with very different copy numbers may be quantifiable by this method, following reverse transcription into cDNA. For most pairs of targets, standard principles of primer design can be followed, with the only additional guidelines being that the primers for the more abundant template may generate a relatively short product (40-80 bp) so that its $T_m$ will be appropriately low (<83° C.), and the primers for the less abundant template may contain the 5' GC-clamps presented here (or similar ones) and generate a short product so that its $T_m$ will be sufficiently high (>90° C.). Furthermore, the nuisance and attendant difficulties, in conventional multiplex QPCR, of having to limit the primer concentrations used to amplify the more abundant template, is eliminated in MMQPCR. The design features of the telg and telc telomere primers herein were used for amplifying short tandem repeats with primers that hybridize to those repeats. In addition to measuring telomere lengths by MMQPCR, mtDNA to nDNA ratios were measured by this approach, and it worked well. Even pairs of templates with similar copy numbers may be studied by this approach by applying primer and thermal profile designs that delay the amplification of one amplicon.

Example 2

MMQPCR of Two Targets of Similar Abundance

In the event that two target nucleic acids are in similar abundance, MMQPCR can be employed. In order to do so, one artificially delays the amplification of one target, while allowing the other target to continue to amplify. For example, the compositions and methods described in Example 1 are used to determine the copy number of a first target nucleic acid and the copy number of a second nucleic acid, when the first and second target nucleic acids are similar in abundance. To do so, one uses the same compositions and methods described above, except for the PCR cycling parameters provided. A thermal cycling profile could be Stage 1: 15 min at 95° C.; Stage 2: 2 cycles of 15 s at 94° C., 15 s at 49° C.; Stage 3: 2 to 6 cycles of 15 s at 88° C., 10 s at 62° C., 15 s at 74° C.; Stage 4: 32 cycles of 15 s at 94° C., 10 s at 62° C., 15 s at 74° C. with signal acquisition, 10 s at 84° C., 15 s at 88° C. with signal acquisition.

Stage 3 above will allow exponential amplification of the telomere product, because it is fully melted at 88 degrees. However, the single copy gene product is fully duplexed at 88 degrees, so the single copy gene primers cannot get onto and amplify the single copy gene product during this Stage 3 cycling.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are specifically incorporated by reference. Nothing herein is to be construed as an admission that the present invention is not entitled to antedate such disclosure by virtue of prior invention.

Those skilled in the art will recognize, or be able to ascertain using no more than routine experimentation, many equivalents to the specific embodiments of the method and compositions described herein. Such equivalents are intended to be encompassed by the following claims.

I claim:

1. A method for determining in a target sample the copy number of a first target nucleic acid and a second target nucleic acid, the method comprising: a) contacting a first target nucleic acid with a first primer set and a second target nucleic acid with a second primer set and adding a single detection label to form a reaction mixture in a homogenous system, wherein one of the primers of the first primer set is blocked from priming the first target nucleic acid and wherein one of the primers of the first primer set is blocked from priming the first target nucleic acid;
wherein the primer blocked from priming the first target nucleic acid comprises a mismatched base at its 3' end" and wherein the first target nucleic acid comprises a tandem repent sequence; b) amplifying by polymerase chain reaction the first target nucleic acid with the first primer set to form a first amplicon having a first melting temperature (Tm) and amplifying by polymerase chain reaction the second target nucleic acid with the second primer set to form a second amplicon having a second Tm, wherein said second Tm is higher than said first Tm; c) during the polymerase chain reaction, determining the amount of the detection label at a first acquisition temperature, wherein said first signal acquisition temperature is below said first Tm; d) increasing the temperature of the reaction mixture to a second signal acquisition temperature and determining the amount of the detection label, wherein said second signal acquisition temperature is above said first TM and below said second Tm; e) repeating steps (b) through (d) at least one time; and f) determining the copy number of said first and said second target nucleic acids.

2. The method of claim 1, wherein the copy number of the first target nucleic acid sequence is greater than the copy number of the second target nucleic acid sequence.

3. The method of claim 1, wherein the amount of the detection label is detected at said first and said second signal acquisition temperatures during each of said amplification steps.

4. The method of claim 1 wherein the difference between the first Tm and the second Tm is at least 4 degrees Celsius.

5. The method of claim 1, wherein at least one of the primers in said first primer set comprises a 5' sequence that includes A and T nucleotides.

6. The method of claim 1, wherein the 3' ends of the primers of the first primer set are complementary to each other.

7. The method of claim 6, wherein one primer of the first primer set is a mismatch primer comprising at least one mismatched nucleotide adjacent to the 3' end of the primer, wherein said nucleotide is not complementary to the target nucleic acid, but is complementary to the 3' terminal nucleotide of the other primer in the first primer set.

8. The method of claim 7, wherein the extension product of the mismatch primer of the first primer set is capable of hybridizing to the other primer in the first primer set.

9. The method of claim 1, wherein the primer blocked from priming the first target nucleic acid comprises a mismatched base at its 3' end.

10. The method of claim 1 wherein the detection label is an intercalating dye.

11. The method of claim 1, wherein the copy number of a first and a second target nucleic acids measures the relative amount of the first nucleic acid as compared to the second nucleic acid.

12. The method of claim 1, wherein the first target nucleic acid is obtained from a sample.

13. The method of claim 1, wherein the copy number of the first target nucleic acid determines the number of tandem repeat sequences present in the sample.

14. The method of claim 1, wherein the copy number of the first target nucleic acid sequence is similar to the copy number of the second target nucleic acid sequence.

15. The method of claim 14, wherein the polymerase chain reaction comprises at least three consecutive stages of cycles, wherein the first stage of cycles of the polymerase chain reaction comprises a polymerase chain reaction wherein the annealing temperature of the polymerase chain reaction is higher than the annealing temperature of the second stage of cycles, wherein the second stage of cycles of the polymerase chain reaction comprises a polymerase chain reaction wherein the annealing temperature of the polymerase chain reaction is lower than the annealing temperature of the first stage of cycles, and wherein the third stage of cycles of the polymerase chain reaction comprises a polymerase chain reaction wherein the annealing temperature of the polymerase chain reaction is lower than the annealing temperature of the first stage of cycles and higher than the annealing temperature of the second stage of cycles.

16. The method of claim 15, wherein only the first amplicon is formed during the first stage of cycles of the polymerase chain reaction.

17. The method of claim 15, wherein only the second amplicon is formed during the second stage of cycles of the polymerase chain reaction.

18. The method of claim 15, wherein both the first and second amplicons are formed during the third stage of cycles of the polymerase chain reaction.

19. The method of claim 15, wherein the amplification step is repeated until the detection label is determined at said second signal acquisition temperature.

20. The method of claim 15, wherein the amount of the detection label is detected at said first and said second signal acquisition temperatures during each of said amplification steps.

21. The method of claim 15, wherein the difference between the first Tm and the second Tm is at least 4 degrees Celsius.

22. The method of claim 15, wherein at least one of the primers in said first primer set comprises a 5' sequence that includes A and T nucleotides.

23. The method of claim 15, wherein the 3' ends of the primers of the first primer set are complementary to each other.

24. The method of claim 23, wherein one primer of the first primer set is a mismatch primer comprising at least one mismatched nucleotide adjacent to the 3' end of the primer, wherein said nucleotide is not complementary to the target nucleic acid, but is complementary to the 3' terminal nucleotide of the other primer in the first primer set.

25. The method of claim 24, wherein the extension product of the mismatch primer of the first primer set is capable of hybridizing to the other primer in the first primer set.

26. The method of claim 15, wherein one of the primers of the first primer set is blocked from priming the first target nucleic acid.

27. The method of claim 26, wherein the primer blocked from priming the first target nucleic acid comprises a mismatched base at its 3' end.

28. The method of claim 15, wherein the detection label is an intercalating dye.

29. The method of claim 15, wherein the copy number of a first and a second target nucleic acids measures the relative amount of the first nucleic acid as compared to the second nucleic acid.

30. The method of claim 15, wherein the first target nucleic acid comprises a tandem repeat sequence.

31. The method of claim 15, wherein the first target nucleic acid is obtained from a sample.

32. The method of claim 31, wherein the copy number of the first target nucleic acid determines the number of tandem repeat sequences present in the sample.

33. The method of claim 1, wherein the amount of detection label determined during the first and said second signal acquisition temperatures are compared to a control.

34. The method of claim 1, wherein the amount of detection label determined during the first and said second signal acquisition temperatures are compared to a control.

* * * * *

UNITED STATES PATENT AND TRADEMARK OFFICE
CERTIFICATE OF CORRECTION

PATENT NO. : 9,689,028 B2
APPLICATION NO. : 13/141429
DATED : June 27, 2017
INVENTOR(S) : Richard M. Cawthon It is certified that error appears in the above-identified patent and that said Letters Patent is hereby corrected as shown below:

In the Claims

In Column 39, Lines 25-28, delete ""wherein one of the primers of the first primer set is blocked from priming the first target nucleic acid; wherein the primer blocked from priming the first target nucleic acid comprises a mismatched base at its 3' end" and".

Signed and Sealed this
Thirteenth Day of August, 2019

Andrei Iancu
*Director of the United States Patent and Trademark Office*

UNITED STATES PATENT AND TRADEMARK OFFICE
CERTIFICATE OF CORRECTION

PATENT NO. : 9,689,028 B2
APPLICATION NO. : 13/141429
DATED : June 27, 2017
INVENTOR(S) : Richard M. Cawthon Page 1 of 1

It is certified that error appears in the above-identified patent and that said Letters Patent is hereby corrected as shown below:

In the Specification

Column 1 Line 14, delete "Portions of the research and inventions disclosed herein may have been made with U. S. Government support under the National Institutes of Health Grant No. 5R21AG030034. The U. S. government has certain rights in this invention." and replace it with the following:
--This invention was made with government support under grant R21 AG030034 awarded by the National Institutes of Health. The government has certain rights in this invention.--

Signed and Sealed this
Tenth Day of September, 2019

Andrei Iancu
*Director of the United States Patent and Trademark Office*

SEQUENCE LISTING

<160> NUMBER OF SEQ ID NOS: 7

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: note = synthetic construct

<400> SEQUENCE: 1 ttaggg					6

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: note = synthetic construct

<400> SEQUENCE: 2
acactaaggt ttgggtttgg gtttgggttt gggttagtgt					40

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: note = synthetic construct

<400> SEQUENCE: 3
tgttaggtat ccctatccct atccctatcc ctatccctaa ca					42

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: note = synthetic construct

<400> SEQUENCE: 4
cggcggcggg cggcgcgggc tgggcggaaa tgctgcacag aatccttg					48

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: note = synthetic construct

<400> SEQUENCE: 5
gcccggcccg ccgcgcccgt cccgccggaa aagcatggtc gcctgtt					47

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: note = synthetic construct

<400> SEQUENCE: 6
cggcggcggg cggcgcgggc tgggcggctt catccacgtt cacccttg					47

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: note = synthetic construct

<400> SEQUENCE: 7
gcccggcccg ccgcgcccgt cccgccggag gagaagtctg ccgtt        45